United States Patent
Charles et al.

(10) Patent No.: US 11,559,513 B2
(45) Date of Patent: Jan. 24, 2023

(54) PTGDR-1 AND/OR PTGDR-2 ANTAGONISTS FOR PREVENTING AND/OR TREATING SYSTEMIC LUPUS ERYTHEMATOSUS

(71) Applicants: INSTITUT NATIONAL DE LA SANTE ET DE LA RECHERCHE MEDICALE (INSERM), Paris (FR); UNIVERSITÉ PARIS DIDEROT—PARIS 7, Paris (FR)

(72) Inventors: Nicolas Charles, Paris (FR); Christophe Pellefigues, Paris (FR)

(73) Assignees: INSTITUT NATIONAL DE LA SANTE ET DE LA RECHERCHE MEDICALE (INSERM), Paris (FR); UNIVERSITE PARIS CITE, Paris (FR)

( * ) Notice: Subject to any disclaimer, the term of this patent is extended or adjusted under 35 U.S.C. 154(b) by 0 days.

(21) Appl. No.: 16/846,611

(22) Filed: Apr. 13, 2020

(65) Prior Publication Data

US 2020/0261413 A1    Aug. 20, 2020

Related U.S. Application Data

(63) Continuation of application No. 16/011,723, filed on Jun. 19, 2018, now abandoned, which is a continuation of application No. 15/549,401, filed as application No. PCT/EP2016/053069 on Feb. 12, 2016, now abandoned.

(30) Foreign Application Priority Data

Feb. 13, 2015  (EP) .................................. 15305222

(51) Int. Cl.
*A61K 31/403* (2006.01)

(52) U.S. Cl.
CPC ........ *A61K 31/403* (2013.01); *A61K 2300/00* (2013.01)

(58) Field of Classification Search
CPC .................................................... A61K 31/403
USPC ......................................................... 514/411
See application file for complete search history.

(56) References Cited

FOREIGN PATENT DOCUMENTS

| WO | WO 2007/042035 | * | 4/2007 |
| WO | WO 2009/085177 | * | 7/2009 |

* cited by examiner

*Primary Examiner* — Marcos L Sznaidman

(57) ABSTRACT

The present invention concerns a PTGDR-1 antagonist, a PTGDR-2 antagonist, a dual PTGDR-1/PTGDR-1 antagonist, or a combination of PTGDR-1 antagonist and PTGDR-2 antagonist, and pharmaceutical compositions containing them, for use for preventing and/or treating SLE.

14 Claims, 14 Drawing Sheets

Figure 1:
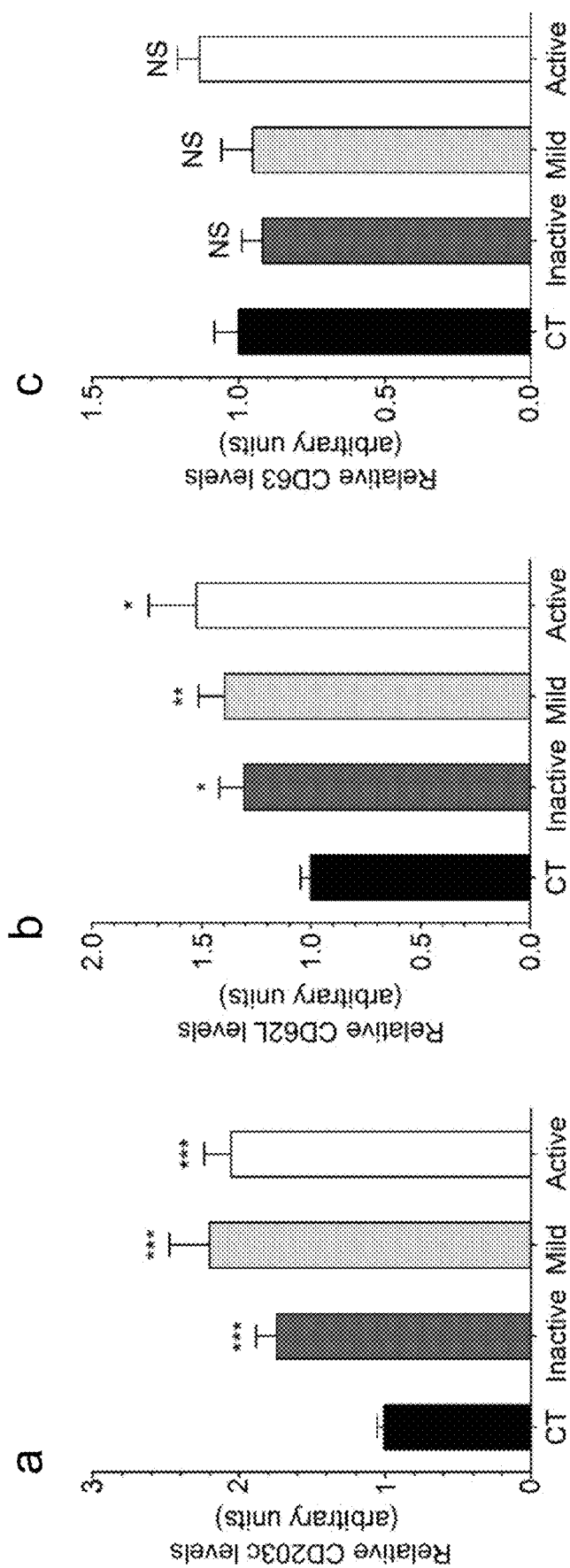

PTGDR-1 AND/OR PTGDR-2 ANTAGONISTS FOR PREVENTING AND/OR TREATING SYSTEMIC LUPUS ERYTHEMATOSUS

CROSS-REFERENCE TO RELATED APPLICATIONS

This application is a continuation application of U.S. Ser. No. 16/011,723 filed Jun. 19, 2018, now U.S. Pat. No. 10,858,306, which itself was a continuation of U.S. Ser. No. 15/549,401 filed Aug. 8, 2017, now abandoned, which was a Rule 371 national stage filing from PCT/EP2016/053069 filed Feb. 12, 2016, and which claimed priority to European Application 15305222.0 filed Feb. 13, 2015.

The present invention concerns a PTGDR-1 antagonist, a PTGDR-2 antagonist, a dual PTGDR-1/PTGDR-1 antagonist, or a combination of PTGDR-1 antagonist and PTGDR-2 antagonist, and pharmaceutical compositions containing them, for use for preventing and/or treating SLE.

Systemic lupus erythematosus (SLE) is a multifactorial autoimmune disease which can affect various organs such as joints and skin and be lethal when kidney involvement (lupus nephritis, LN) is not controlled. If considered as a B cell disease, both innate and adaptive immune systems are dysregulated during SLE and synergize to amplify the production of the main lupus pathogenic factors which are autoantibodies mostly directed against nuclear antigens (ANA) such as double stranded DNA (dsDNA). Once aggregated to their antigens and complement factors, these autoantibodies will form circulating immune complexes mediating a chronic inflammation when deposited in the targeted organ. Flares of the disease are usually controlled by strong immunosuppressive treatments and high dose of corticosteroids. Recent clinical trials aimed to decrease autoantibody production in subjects with SLE by directly targeting the B cell compartment but failed to demonstrate sufficient efficacy. Developing new therapeutic strategies to prevent flares to occur represents a big challenge for the biomedical community.

Basophils are one of the less represented circulating leukocytes and are well known for their involvement in allergic and parasitic diseases. During the past decade, basophils were shown having powerful immune regulatory functions despite their weak representation). It was previously shown that basophils were able to support plasma cell survival and antibody production in vivo while expressing some B cell activating factors such as BAFF (B cell activating factor), CD40L (CD40 ligand or CD154), interleukin (IL)-4 and IL-6 ((Voehringer, D., Nat. Rev. Immunol. 13, 362-375 (2013); Charles, N. et al., Nat. Med. 16, 701-707 (2010)). This immunomodulatory role is associated with their ability to accumulate in secondary lymphoid organs (SLOs) where they can help T and B cells in differentiation and maturation (Charles, N. et al., Nat. Med. 16, 701-707 (2010); Leyva-Castillo, J. M., et al., Nat Commun 4, 2847 (2013); Otsuka, A., et al., Nat Commun 4, 1739 (2013)). Mechanisms leading to SLOs basophil accumulation are poorly understood.

C—X—C motif Ligand 12 (CXCL12) is a chemokine secreted mostly by stromal cells from bone marrow, peritoneal cavity, SLOs, and kidneys. CXCL12 acts as a homeostatic chemokine by regulating mesenchymal stem cells, B cells and neutrophils physiological distribution via its specific interaction with C—X—C motif Receptor 4 (CXCR4). CXCL12 overexpression occurs in inflamed tissues and is pathogenic in cancer and lupus nephritis among other diseases (Wang, A., et al., J. Immunol. 182, 4448-4458 (2009); Balabanian, K., et al., J. Immunol. 170, 3392-3400 (2003); Hummel, S., Van Aken, H. & Zarbock, A., Curr. Opin. Hematol. 21, 29-36 (2014)).

Prostaglandin $D_2$ ($PGD_2$) is produced from arachidonic acid by cyclooxygenases and tissue-specific $PGD_2$ synthases (PGDS). $PGD_2$ contributes to various homeostatic functions and is involved in the onset and resolution of inflammation through its interactions with the two known $PGD_2$ receptors (PTGDRs): PTGDR-1 (or DP, D prostanoid receptor) and PTGDR-2 (or DP-2, also known as chemoattractant receptor-homologous molecule expressed on T helper type 2 ($T_H2$) cells, CRTH2). Basophils express the highest level of the ubiquitous PTGDR-1 among peripheral blood leukocytes. PTGDR-2 expression is more restricted and mediates activation and chemotaxis of basophils, eosinophils and $T_H2$ $CD4^+$ T cells. The effects of these two receptors can be competitive or cooperative. $PGD_2$ has been involved in allergic and pulmonary diseases, ulcerative colitis, and renal fibrosis. Lipocalin-type-PGDS (L-PGDS) was recently found to be expressed de novo in inflamed kidneys (Nagata, N., et al., FEBS J 276, 7146-7158 (2009) and in the urine of active LN patients (Suzuki, M., et al., Pediatr. Res. 65, 530-536 (2009); Somparn, P., et al., J. Proteomics 75, 3240-3247 (2012)).

However, the $PGD_2$/PTGDRs axis has not been characterized in SLE.

In this respect, the international patent application WO 2009/085177 has disclosed dual PTGDR-1/PTGDR-2 antagonists and suggested that these antagonists could be useful in the prevention and/or treatment of a list of diseases including SLE. However the only therapeutic effect concretely evaluated in this document is against asthma. The proposed prevention and/or treatment of SLE is not substantiated.

The inventors recently showed that basophils were involved in the development of LN both in a spontaneous murine SLE model ($Lyn^{-/-}$ mice) and in a small cohort of 42 patients by accumulating in SLOs where they support autoreactive T and B cells through an IgE and IL-4 dependent pathway (Charles, N. et al., Nat. Med. 16, 701-707 (2010)). Since the production of potent basophil activators or chemo-attractants is known to be dysregulated during lupus pathogenesis (Pellefigues, C. & Charles, N., Curr. Opin. Immunol. 25, 704-711 (2013)), mechanisms underlying basophil recruitment to SLOs during SLE were explored.

The inventors have now identified two new pathways by which basophils get activated during flares of the disease.

Tissue chronic inflammation is leading to the secretion of basophil activating factors which systemic concentrations are dysregulated during lupus. In a new larger cohort of individuals with SLE, the inventors confirmed that basopenia was a characteristic of SLE patients and was correlated with disease activity. Moreover, as compared to other renal diseases, basopenia was specific of lupus nephritis. This basopenia was associated with a specific expression pattern on basophils of some known and new activation markers. Indeed, CXCR4 expression at the protein level and on the surface of basophils was markedly increased in active patients and associated with basopenia.

The inventors found that disease activity and basopenia were tightly linked together and to $PGD_2$/PTGDRs and CXCL12/CXCR4 axes.

Beyond their altered expression pattern on active lupus subject basophils, CXCR4 and CD164 led to a dramatically increased sensitivity of SLE basophils to CXCL12-mediated migration ex vivo. In non-sterile peritonitis patients, the inventors demonstrated that migrated basophils were dramatically overexpressing CXCR4 as compared to their "non-migrated" blood basophil counterparts, strongly suggesting that human CXCR4+ basophil extravasation and migration could be induced in vivo by CXCL12, leading to a peripheral basopenia. In mice, CXCL12 induced a redistribution of CXCR4+ basophils at the injection site and in the corresponding draining lymph nodes, demonstrating basophil migration capability to CXCL12 in vivo. These migration abilities, both in human and mice, were enabled in vivo and ex vivo by the $PGD_2$/PTGDRs axis.

Furthermore, the inventors demonstrated that $PGD_2$ synthesis was increased in SLE subjects and associated with basopenia. This $PGD_2$-mediated CXCR4-dependent basophil migration was, at least partially, due to an autocrine effect of $PGD_2$ upon its synthesis by basophils themselves ex vivo, resulting in an externalization of CXCR4. In particular, both in subjects with SLE and in $Lyn^{-/-}$ mice, the inventors found that $PGD_2$ (the $PGD_2$/PTGDRs axis) was enhancing CXCR4-dependent basophil recruitment to SLOs during lupus, explaining the flare of the disease observed with repeated $PGD_2$ injections in lupus-prone mice. These data underline the CXCR4-mediated pathogenic effect of $PGD_2$ during lupus pathogenesis, identifying both axes as putative therapeutic targets.

The inventors thus concluded that altering these axes in SLE patients using PTGDRs specific antagonists should break the basophil-dependent autoantibody production and kidney inflammation as showed in the $Lyn^{-/-}$ lupus-like mouse model, and should limit SLE flares and long term organ damages by preventing basophil homing to SLOs.

The inventors demonstrated that antagonizing PTGDRs in vivo in a lupus-like mouse model prevented the CXCR4-dependent basophil recruitment in SLOs without impacting other cell type proportions but the short lived plasma cells. This treatment achieved to dampen short-lived plasma cell number, renal inflammation, and autoantibodies titers in only 10 days.

Definitions

The terms "lupus" or "systemic lupus erythematosus" or "SLE" are used in their customary meaning herein and include an autoimmune disorder characterized by the presence of autoantibodies, rash, oral ulcers, serositis, neurological disorders, low blood cell counts, joint pain and swelling. Tests used to diagnose include antibody tests (e.g., Antinuclear antibody (ANA) panel, Anti-double strand DNA (dsDNA), Antiphospholipid antibodies, Anti-Smith antibodies); CBC to show low white blood cells, hemoglobin, or platelets; chest x-ray showing pleuritis or pericarditis; kidney biopsy; urinalysis to show blood, casts, or protein in the urine.

By "lupus nephritis" is meant a disorder characterized by an inflammation of the kidney caused by systemic lupus erythematosus (SLE). Lupus nephritis is characterized by IgM-, IgG-, and IgA-containing immune complexes deposited in the glomeruli. These immune complexes are formed by autoantibodies with specificity to nuclear components (antinuclear antibodies (ANA)) or to nucleic acids (such as double-stranded DNA (dsDNA)).

Accordingly, as used herein, prevention and/or treatment of systemic lupus erythematosus or "SLE" encompasses prevention and/or treatment of lupus nephritis.

In the context of the invention, the term "treating" or "treatment", refers to a therapeutic use (i.e. on a subject having a given disease) and means reversing, alleviating, inhibiting the progress of one or more symptoms of such disorder or condition. Therefore, treatment does not only refer to a treatment that leads to a complete cure of the disease, but also to treatments that slow down the progression of the disease and/or prolong the survival of the subject.

By "preventing" is meant a prophylactic use (i.e. on a subject susceptible of developing a given disease).

"Prostaglandin D2" or "$PDG_2$" is 9α,15S-dihydroxy-11-oxo-prosta-5Z,13E-dien-1-oic acid (IUPAC name) (CAS number:41598-07-6).

"PTGDR-1" or "DP" or "D prostanoid receptor" is a receptor for prostaglandin D2 and its activity is mainly mediated by G(s) proteins that stimulate adenylate cyclase, resulting in an elevation of intracellular cAMP. An exemplary sequence of human PTGDR-1 protein is available in the UniProt database, under accession number Q13258 (in particular Q13258-1:isoform 1, Entry version 133 of 7 Jan. 2015). A complete mRNA sequence encoding PTGDR-1 is available in Genbank under accession number EF577397.1 (release: 122; issue date: 21 Nov. 2014).

"PTGDR-2" or "chemoattractant receptor-homologous molecule expressed on T helper type 2 (TH2) cells" or "CRTH2" or "DP2" is a G-protein-coupled receptor for prostaglandin D2 that is preferentially expressed in CD4+ effector T helper 2 (Th2) cells. An exemplary sequence of human PTGDR-2 protein is available in the UniProt database, under accession number Q9Y5Y4 (Entry version 120 of 7 Jan. 2015). A complete mRNA sequence encoding PTGDR-2 is available in Genbank under accession number AY507142.1 (release: 122; issue date: 21 Nov. 2014).

As used herein, the term "antagonist" refers to any molecule that partially or fully blocks, inhibits, reduces or neutralizes expression and/or biological activity of a target and/or signalling pathway.

"PTGDR-1 antagonist" refers to a molecule that partially or fully blocks, inhibits, neutralizes, or interferes with the expression and/or biological activities of a PTGDR-1 protein. This includes, but is not limited to, blocking, inhibiting, reducing, or interfering with $PDG_2$/PTGDR-1 interactions. PTGDR-1 antagonists include for instance a $PDG_2$ neutralising antibody, i.e. an antibody which binds to $PDG_2$ and prevents $PDG_2$ binding to PTGDR-1.

"PTGDR-2 antagonist" refers to a molecule that partially or fully blocks, inhibits, neutralizes, or interferes with the expression and/or biological activities of a PTGDR-2 protein. This includes, but is not limited to, blocking, inhibiting, reducing, or interfering with $PDG_2$/PTGDR-2 interactions. PTGDR-2 antagonists include for instance a $PDG_2$ neutralising antibody, i.e. an antibody which binds to $PDG_2$ and prevents $PDG_2$ binding to PTGDR-2.

Suitable antagonist molecules specifically include, but are not limited to biological molecules such as a protein, polypeptide, peptide, antibody, antibody fragment, aptamers, antisense, interfering RNAs, or non-biological large or small molecules (less than 10 kDa), in particular small organic molecules.

The antagonist may be an inhibitor of PTGDR-1 or PTGDR-2 gene expression. Inhibitors of gene expression include antisense oligonucleotides and interfering RNA (iRNA).

The term "iRNA" include double-stranded RNA, single-stranded RNA, isolated RNA (partially purified RNA, essentially pure RNA, synthetic RNA, recombinantly produced RNA), as well as altered RNA that differs from naturally occurring RNA by the addition, deletion, substitution and/or alteration of one or more nucleotides. Such alterations can include addition of non-nucleotide material, such as to the end(s) of the RNA or internally (at one or more nucleotides of the RNA). Nucleotides in the iRNA molecules can also comprise non-standard nucleotides, including non-naturally occurring nucleotides or deoxyribonucleotides. Collectively, all such altered iRNA compounds are referred to as analogs or analogs of naturally-occurring RNA. A iRNA needs only be sufficiently similar to natural RNA that it has the ability to mediate RNA interference. As used herein the phrase "mediate RNA Interference" refers to and indicates the ability to distinguish which mRNA are to be affected by the RNA interference machinery or process. RNA that mediates RNA interference interacts with the RNA interference machinery such that it directs the machinery to degrade particular mRNAs or to otherwise reduce the expression of the target protein. In one embodiment, iRNA molecules direct cleavage of specific mRNA to which their sequence corresponds. It is not necessary that there be perfect correspondence of the sequences, but the correspondence must be sufficient to enable the iRNA to direct RNA interference inhibition by cleavage or lack of expression of the target mRNA. The iRNA molecules may comprise an RNA portion and some additional portion, for example a deoxyribonucleotide portion. The total number of nucleotides in the RNA molecule is suitably less than 49 in order to be effective mediators of RNA interference. In preferred RNA molecules, the number of nucleotides is 16 to 29, more preferably 18 to 23, and most preferably 21-23.

As indicated above, the term iRNA includes but is not limited to siRNAs, shRNAs, miRNAs, dsRNAs, and other RNA species that can be cleaved in vivo to form siRNAs.

A "short interfering RNA" or "siRNA" comprises a RNA duplex (double-stranded region) and can further comprises one or two single-stranded overhangs, 3' or 5' overhangs.

A "short hairpin RNA (shRNA)" refers to a segment of RNA that is complementary to a portion of a target gene (complementary to one or more transcripts of a target gene), and has a stem-loop (hairpin) structure.

"MicroRNAs" or "miRNAs" are endogenously encoded RNAs that are about 22-nucleotide-long, that post-transcriptionally regulate target genes and are generally expressed in a highly tissue-specific or developmental-stage-specific fashion. One can design and express artificial miRNAs based on the features of existing miRNA genes. The miR-30 (microRNA 30) architecture can be used to express miRNAs (or siRNAs) from RNA polymerase II promoter-based expression plasmids (Zeng et al, 2005, Methods enzymol. 392:371-380). In some instances the precursor miRNA molecules may include more than one stem-loop structure. The multiple stem-loop structures may be linked to one another through a linker, such as, for example, a nucleic acid linker, a miRNA flanking sequence, other molecules, or some combination thereof.

Anti-sense oligonucleotides are non-enzymatic nucleic acid molecules that bind to target RNA by means of RNA-RNA or RNA-DNA or RNA-PNA (protein nucleic acid; Egholm et al, 1993 Nature 365, 566) interactions and alter the activity of the target RNA. Typically, anti-sense molecules are complementary to a target sequence along a contiguous sequence of the antisense molecule. In addition, anti-sense DNA can be used to target RNA by means of DNA-RNA interactions, thereby activating RNase H, which digests the target RNA in the duplex.

The term "antibody" refers to immunoglobulin molecules and immunologically active portions of immunoglobulin molecules, i.e., molecules that contain an antigen binding site which immunospecifically binds an antigen. As such, the term antibody encompasses not only whole antibody molecules, but also antibody fragments as well as variants (including derivatives) of antibodies and antibody fragments. In particular, the antibody according to the invention may correspond to a polyclonal antibody, a monoclonal antibody (e.g. a chimeric, humanized or human antibody), a fragment of a polyclonal or monoclonal antibody or a diabody.

"Antibody fragments" comprise a portion of an intact antibody, preferably the antigen binding or variable region of the intact antibody. Examples of antibody fragments include Fv, Fab, F(ab')$_2$, Fab', Fd, dAb, dsFv, scFv, sc(Fv)$_2$, CDRs, diabodies and multi-specific antibodies formed from antibodies fragments.

"Aptamers" are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., Science, 1990, 249(4968):505-10. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., Clin. Chem., 1999, 45(9): 1628-50. Peptide aptamers consists of a conformationally constrained antibody variable region displayed by a platform protein, such as *E. coli* Thioredoxin A that are selected from combinatorial libraries by two hybrid methods (Colas et al., Nature, 1996, 380, 548-50).

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of").

Furthermore the indefinite article "a" or "an" does not exclude a plurality.

DESCRIPTION OF THE INVENTION

The invention relates to a PTGDR-1 antagonist for use in a method for preventing and/or treating SLE. The invention also relates to the use of a PTGDR-1 antagonist for the manufacture of a medicament for preventing and/or treating SLE. The invention further relates to a method for preventing and/or treating SLE in a patient in need thereof, wherein said method comprises administering said patient with a PTGDR-1 antagonist.

According to another aspect, the invention relates to a PTGDR-2 antagonist for use in a method for preventing and/or treating SLE. The invention also relates to the use of a PTGDR-2 antagonist for the manufacture of a medicament for preventing and/or treating SLE. The invention further relates to a method for preventing and/or treating SLE in a patient in need thereof, wherein said method comprises administering said patient with a PTGDR-2 Antagonist.

PTGDR-1 antagonists According to an embodiment, said PTGDR-1 antagonist is a small molecule antagonist.

Numerous PTGDR-1 antagonists have been described in the art.

Said small molecule antagonist is in particular selected from the group consisting of compounds of formulae I to VI as disclosed hereafter:

(i) Compounds of formula (I) as described in patent application WO03062200:

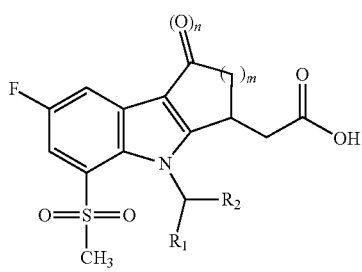

(I)

and pharmaceutically acceptable salts thereof, wherein
n is 0 or 1; m is 1, 2 or 3; $R_1$ is H, $C_1$-$C_3$ alkyl, halogenated $C_1$-$C_3$ alkyl or cyclopropyl; $R_2$ is 4-chlorophenyl or 2,4,6-trichlorophenyl.

Preferably, the compounds of formula I have the stereo-configuration shown below (i.e. the chiral center has the R configuration):

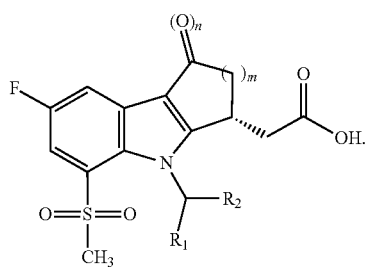

(formula II)

In particular, the compound of formula I or II is laropiprant, i.e. (−)-[4-(4-chlorobenzyl)-7-fluoro-5-(methane-sulfonyl)-1,2,3,4-tetrahydrocyclopenta[b]indol-3-yl]acetic acid and pharmaceutically acceptable salts thereof:

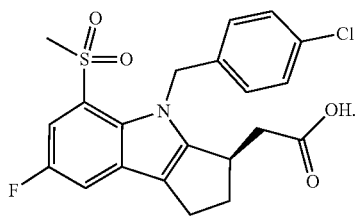 [SMILES: CS(=O)(=O)c1cc(F)cc2c3c(n(Cc4ccc(Cl)cc4)c12)[C@@H](CC(=O)O)CC3]

Laropiprant is approved by the FDA to inhibit the flushing induced by niacin to treat dyslipidemias.

(ii) Compounds disclosed in patent application WO0179169: i.e. 2-[(1R)-9-(4-chlorobenzyl)-8-((R)-methyl-sulfinyl)-2,3,4,9-tetrahydro-1H-carbazol-1-yl] acetic acid, or a pharmaceutically acceptable salt thereof, or 2-[(1R)-9-(4-chlorobenzyl)-8-((S)-methyl-sulfinyl)-2,3,4,9-tetrahydro-1H-carbazol-1-yl] acetic acid, or a pharmaceutically acceptable salt thereof;

(iii) Compounds disclosed in patent application WO0208186:

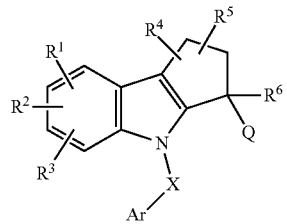

(formula III)

and pharmaceutically acceptable salts, hydrates and esters thereof, wherein:

R1, R2 and R3 are each independently selected from the group consisting of: (1) hydrogen, and (2) Rc, R4 and R5 are each independently selected from the group consisting of: (1) H, (2) F, (3) CN, (4) C1-6alkyl, (5) ORa, and (6) S(O)$_n$C1-6alkyl, wherein each of said alkyl group is optionally substituted with halogen, or R4 and R5 on the same carbon atom represent an oxo, or R4 and R5 on the same carbon atom or on adjacent carbon atoms taken together form a 3- or 4-membered ring containing 0 or 1 heteroatom selected from N, S, or O optionally substituted with one or two groups selected from F, $CF_3$ and $CH_3$;

R6 is selected from the group consisting of: (1) H, (2) C1-6alkyl optionally substituted with one to six groups independently selected from ORa and halogen, and (3) heterocyclyl optionally substituted with one to four halogen; or R5 and R6 attached on adjacent carbon atoms together form a 3- or 4-membered ring containing 0 or 1 heteroatom selected from N, S, or O optionally substituted with one or two groups selected from F, $CF_3$ and $CH_3$;

X is selected from the group consisting of: C═O, $SO_2$, and C1-4alkyl wherein said alkyl is optionally substituted with one to six halogen;

Ar is aryl or heteroaryl each optionally substituted with one to four groups independently selected from Rc;

Q is C1-6alkyl optionally substituted with one to six groups independently selected from: (1) halogen, (2) aryl, (3) heteroaryl, (4) OH, (5) OC1-6alkyl, (6) COOH, (7) CONRaRb, (8) C(O)NSO$_2$R7, (9) tetrazolyl, wherein aryl, heteroaryl and alkyl are each optionally substituted with one to six groups independently selected from halogen, $CF_3$, and COOH; or Q and R6 together form a 3- or 4-membered ring optionally containing a heteroatom selected from N, S, and O, and optionally substituted with one or two groups independently selected from: (1) halogen, (2) oxo, (3) ORa, (4) COOH, (5) C(O)NHSO$_2$R7, and (6) tetrazolyl, R7 is selected from the group consisting of: (1) C1-6alkyl optionally substituted with one to six halogen, (2) aryl, and (3) heteroaryl, wherein said aryl and heteroaryl are optionally substituted with halogen, OC1-5alkyl, C1-5alkyl and wherein said alkyl is optionally substituted with one to six halogen;

Ra and Rb are independently selected from hydrogen and C1-6alkyl optionally substituted with one to six halogen;

Rc is (1) halogen, (2) CN, (3) C1-6alkyl optionally substituted with one to six groups independently selected from halogen, NRaRb, C(O)Ra, C(ORa)RaRb, and ORa, (4) C2-6alkenyl optionally substituted with one to six groups independently selected from halogen and ORa, (5) heterocyclyl, (6) aryl, (7) heteroaryl, (8) C(O)Ra, (9) C(ORa)RaRb (10) C(O)ORa, (11) CONRaRb, (12) OCONRaRb, (13) S(O)$_n$R7, (14) NRaC(O)OC1-6alkyl, wherein alkyl is optionally substituted with one to six halogen and (15) S(O)$_n$NRaRb, wherein heterocyclyl, aryl, heteroaryl are optionally substituted with one to four groups independently selected from halogen; n is 0, 1 or 2.

(iv) Compounds disclosed in patent application WO03062200:

(formula IV)

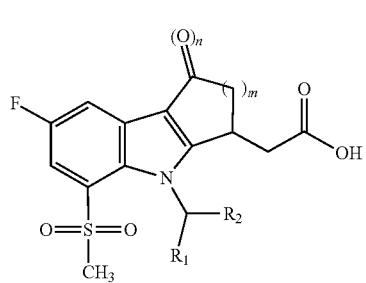

and pharmaceutically acceptable salts thereof, wherein
n is 0 or 1; m is 1, 2 or 3; $R_1$ is H, $C_1$-$C_3$ alkyl, halogenated $C_1$-$C_3$ alkyl or cyclopropyl; $R_2$ is 4-chlorophenyl or 2,4,6-trichlorophenyl.

In particular, a compound of formula IV is (−)-[4-(4-chlorobenzyl)-7-fluoro-5-(methanesulfonyl)-1,2,3,4-tetrahydrocyclopenta[b]indol-3-yl]acetic acid or a pharmaceutically acceptable salt thereof, i.e.:

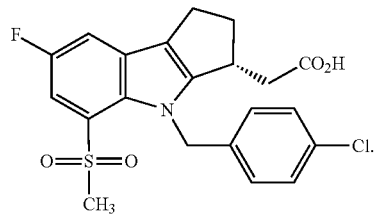 [SMILES: CS(=O)(=O)c1cc(F)cc2c3c(n(Cc4ccc(Cl)cc4)c12)[C@@H](CC(=O)O)CCC3]

(v) Compounds disclosed in patent application WO2004103970:

(formula V)

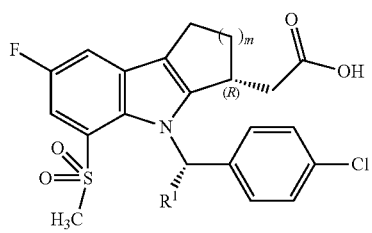

and pharmaceutically acceptable salts thereof, wherein m is 1 or 2, and $R_1$ is $C_1$-$C_3$ alkyl optionally substituted with 1 to 5 halogen atoms.

Said compound of formula V is in particular selected from the group consisting of:

[(3R)-4-[(1S)-1-(4-chlorophenyl)ethyl]-7-fluoro-5-(methylsulfonyl)-1,2,3,4-tetrahydrocyclopenta[b]indol-3-yl] acetic acid and pharmaceutically acceptable salts thereof,

[(1R)-9-[(1 S)-1-(4-chlorophenyl)ethyl]-6-fluoro-8-(methylsulfonyl)-2,3,4,9-tetrahydro-1H-carbazol-1-yl] acetic acid and pharmaceutically acceptable salts thereof,

[(1R)-9-[(1R)-1-(4-chlorophenyl)-2-fluoroethyl]-6-fluoro-8-(methylsulfonyl)-2,3,4,9-tetrahydro-1H-carbazol-1-yl] acetic acid and pharmaceutically acceptable salts thereof, and

[(1R)-9-[(1R)-1-(4-chlorophenyl)-2,2-difluoroethyl]-6-fluoro-8-(methylsulfonyl)-2,3,4,9-tetrahydro-1H-carbazol-1-yl] acetic acid and pharmaceutically acceptable salts thereof.

(vi) [2-(oxazol-2-yl)-5-(4-{[(propan-2-yl)oxy]phenylsulfonyl}piperazin-1-yl)phenoxy]acetic acid (formula VI)

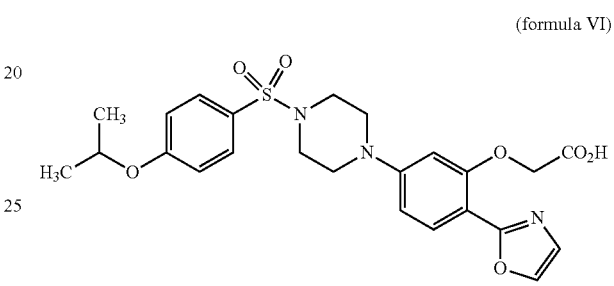

or a pharmaceutically acceptable salt thereof, as described in EP2762141. This compound can be synthesized in accordance with a known method, for example, a method as described in WO 2007/037187 or WO 2008/123349.

Exemplary PTGDR-1 antagonists include, but are not limited to, compounds described as having PGD2 antagonizing activity in PCT Published Applications WO97/00853, WO98/25919, WO01/66520, WO02/094830, WO03/022814, WO03/078409, and WO2004/103370; European Patent Applications EP945450, EP944614, and EP 1305286; and U.S. Application Publ. No. 20040220237, 20070244107, and 20080194600, all of which are hereby incorporated by reference in their entirety.

According other embodiments, the PTGDR-1 antagonist is biological molecule antagonist.

For instance said PTGDR-1 antagonist is an antibody, preferably monoclonal antibody, or antibody fragment, or aptamer directed against PTGDR-1. Methods of producing polyclonal or monoclonal antibodies are readily available to the skilled person.

Said PTGDR-1 antagonist may also be an antisense, or interfering RNA inhibiting PTGDR-1 expression.

In an embodiment said PTGDR-1 antagonist is an anti-sense oligonucleotide, in particular an anti-sense oligonucleotide comprising or consisting of one of the sequence SEQ ID NO:4415 to SEQ ID No:5483, as disclosed in the international patent application published as WO02/081628.

PTGDR-2 Antagonists

According to an embodiment, said PTGDR-2 antagonist is a small molecule antagonist.

Numerous PTGDR-1 antagonists have been described in the art.

In some embodiments, a PTGDR-2 antagonist is selected from the group consisting of:

(i) Compounds disclosed in WO2013088109:

(formula VII)

wherein
R1 is C1-C6 alkyl;
R2 is halogen;
R3 is aryl or heteroaryl optionally substituted with one or more substituents selected from halo, OH, CN, R6, COR6, CH2R6, OR6, SR6, SO$_2$R6, or SO$_2$YR6;
R6 is C1-C6 alkyl, C3-C8 cycloalkyl, heterocyclyl, aryl, or heteroaryl, any of which may optionally be substituted with one or more substituents selected from halo, OH, CN, NO2, C1-C6 alkyl, or O(C1-C6 alkyl); and
Y is NH or a straight or branched C1-C4 alkylene chain;
R4 is H or C1-C4 alkyl; and
R5 is hydrogen, C1-C6 alkyl, aryl, (CH2)$_m$OC(=O)C1-C6 alkyl, ((CH2)$_m$O)$_n$CH2CH2X, (CH2)$_m$N(R7)$_2$, or CH((CH2)$_m$O(C=O)R8)$_2$;
m is 1 or 2;
n is 1-4;
X is OR7 or N(R7)2;
R7 is hydrogen or methyl;
R8 is C1-C,8 alkyl;
or a pharmaceutically acceptable salt, hydrate, solvate, or complex thereof, (ii) cycloalkano(1,2-b)indole-sulfonamides as described in EP0242518B1

(formula VIII)

wherein R1 is H, fluorine, methyl, methoxy, benzyloxy, or hydroxyl,
R2 is phenyl which is substituted by fluorine, chlorine, trifluoromethyl, methyl, ethyl, propyl, isopropyl, or methoxy, and
Y is 0 or 1,
or pharmaceutically acceptable salts thereof.

In particular, a compound of formula VIII is selected from the group consisting of:

Ramatroban ((R)-3-[[(4-fluorophenyl)sulphonyl]amino]-1,2,3,4-tetrahydro-9H-carbazole-9-propanoic acid):

or a thermodynamically stable form thereof as described in EP1051398, and analogs of Ramatroban, in particular TM30642 (3-{3-[(4-fluoro-benzenesulfonyl)-methyl-amino]1,2,3,4-tetrahydro-carbazol-9-yl{-propionic acid):

TM30643 ([3-(4-fluoro-benzenesulfo-nylamino)-1,2,3,4-tetrahydro-carbazol-9-yl]-acetic acid):

and

TM30089 (also called CAY10471) (CAS 627865-18-3: 2-[3-[(4-fluorophenyl)sulfonyl-methylamino]-1,2,3,4-tetrahydrocarbazol-9-yl]acetic acid):

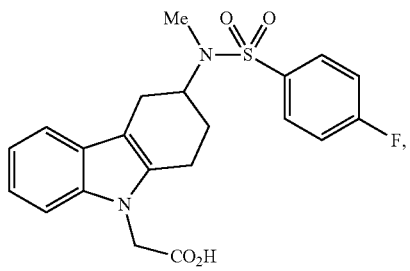 [SMILES: CN(C1CCc2c(c3ccccc3n2CC(=O)O)C1)S(=O)(=O)c1ccc(F)cc1]

(iii) OC000549 (5-fluoro-2-methyl-3-(2-quinolinylmethyl-1H-indole-1-acetic acid)

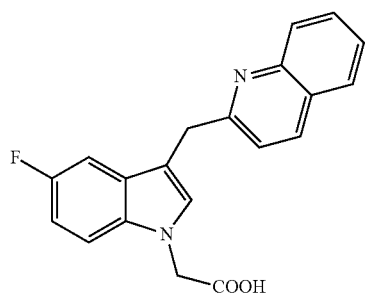 [SMILES: O=C(O)Cn1cc(Cc2ccc3ccccc3n2)c2cc(F)ccc21]

(iv) Setipiprant

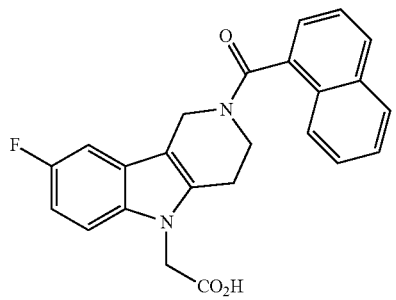 [SMILES: O=C(O)Cn1c2c(c3cc(F)ccc31)CN(C(=O)c1cccc3ccccc13)CC2]

and

AZD1981 (4-(actylamino)-3-[(4-chlorophenyl)thio]-2-methyl-1H-indole-1-acetic acid).

Additional PTGDR-2 antagonists can be found in the following publications: EP1, 170,594, EP1,435,356 WO2003/066046, WO2003/066047, WO2003/097042, WO2003/097598, WO2003/101961, WO2003/101981, WO2004/007451, WO2004/032848, WO2004/035543, WO2004/106302, WO2005/019171, WO2005/054232, WO2005/018529, WO2005/040112, GB2,407,318, WO2005/040114, WO2005/044260, WO2005/095397, WO2005/100321, WO2005/102338, WO2005/123731, WO2006/034419, WO2006/095183, WO2007/107772, WO2008024746, U.S. Pat. No. 7,405,215, each of which is hereby incorporated by reference in its entirety.

According other embodiments, the PTGDR-2 antagonist is biological molecule antagonist.

For instance said PTGDR-2 antagonist is an antibody, preferably monoclonal antibody, or antibody fragment, or aptamer directed against PTGDR-2. In an embodiment said PTGDR-2 antagonist is an antibody depleting PTGDR-2 expressing cells such as described in the international patent application WO2014144865.

Said PTGDR-2 antagonist may also be an antisense, or interfering RNA inhibiting PTGDR-2 expression.

Dual PTGDR-1/PTGDR-2-Antagonists

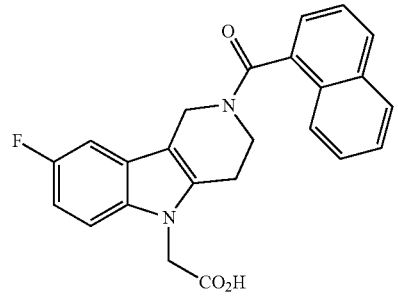 [SMILES: O=C(O)Cn1c2c(c3cc(F)ccc31)CN(C(=O)c1cccc3ccccc13)CC2]

As used herein, a dual PTGDR-1/PTGDR-2 antagonist is an antagonist for which the ratio of antagonist activity against PTGDR-1 and PTGDR-2, respectively, is from 1:10 to 10:1, in particular from 1:50 to 50:1, preferably from 1:100 to 100:1, still preferably from 1:250 to 250:1.

Dual PTGDR-1/PTGDR-2 antagonists that can be used in the frame of the invention include, for instance, the compounds described in patent application WO 2009/085177:

(formula VI)

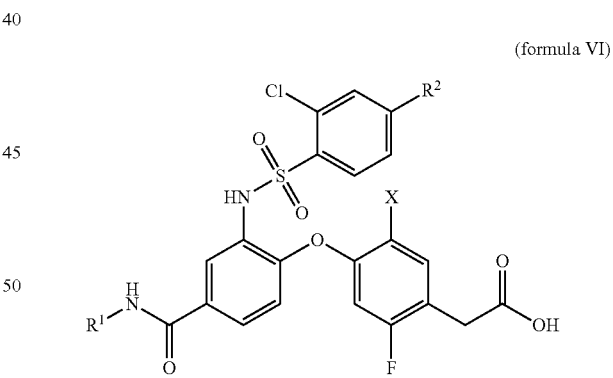

and pharmaceutically acceptable salts thereof, wherein R1 is alkyl or cycloalkyl; R2 is halo, alkyl, haloalkyl, alkoxy, haloalkoxy or cycloalkyl; and X is chloro or fluoro.

Preferably, said compound of formula VI is AMG 853 (2-(4-(4-(tert-butylcarbamoyl)-2-(2-chloro-4-cyclopropylphenyl sulfonamido)phenoxy)-5-chloro-2-fluorophenyl) acetic acid):

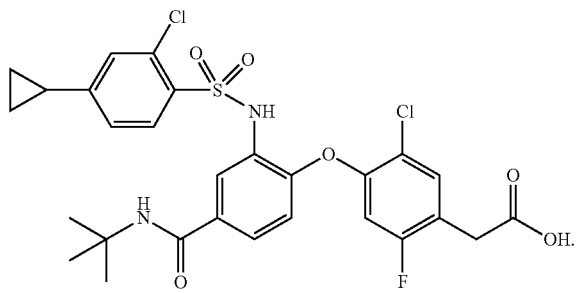 [SMILES: CC(C)(C)NC(=O)c1ccc(Oc2cc(F)c(CC(=O)O)cc2Cl)c(NS(=O)(=O)c2ccc(C3CC3)cc2Cl)c1]

AMG 853, as well as a method of preparing this compound, are also described in Liu et al., ACS Med Chem Lett. 2011 Mar. 2; 2(5):326-30.

However, in an embodiment the dual PTGDR-1/PTGDR-2 antagonists of formula VI are excluded from the scope of the invention.

Characterisation of the antagonistic activity of a molecule towards PTGDR-1 and/or PTGDR-2 can be performed, for instance, by methods described in Liu et al., ACS Med Chem Lett. 2011 Mar. 2; 2(5):326-30. These methods include:

(i) Determining the molecule's $IC_{50}$ towards PTGDR-1 and/or PTGDR-2. This can be performed for instance on HEK-293 cells stably expressing human PTGDR-1 or PTGDR-2. To measure binding, detectably labelled $PGD_2$, e.g. [$^3$H]-$PGD_2$, is incubated together with HEK-293 (PTGDR-1 or PTGDR-2) cells in the presence of increasing concentrations of the molecule to be assayed. After incubation, cells are washed, and the amount of labelled $PGD_2$ that remained bound to the cells is measured by an appropriate method (for instance scintillation counting if [$^3$H]-$PGD_2$), and the concentration of compounds required to achieve a 50% inhibition of [$^3$H]-$PGD_2$ binding (the $IC_{50}$) was determined. The binding buffer contains either 0.5% BSA (buffer binding) or 50% human plasma (plasma binding).

(ii) Determining the molecule's affinity for PTGDR-1. This can be performed for instance on whole blood drawn into acid-citrate-dextrose vacutainer tubes, treated with test molecule or DMSO, and then stimulated with a dose response of $PGD_2$. Cells are then lysed, and cAMP is measured using a competitive ELISA. Comparison of the dose response to $PGD_2$ in samples containing DMSO only and samples containing with test molecule is used in determining $K_b$ using the Schild equation (Schild H O. PA2, a new scale for the measurement of drug antagonism. Brit J Pharmacol 1947; 2:189-206).

(i) Determining the molecule's affinity for PTGDR-2. This can be performed for instance on whole blood drawn into acid-citrate-dextrose anticoagulated tubes, treated with test molecule or DMSO, and then stimulated with a dose response of $PGD_2$. Fluorochrome conjugated antibodies are used to label PTGDR-2 positive granulocytes, and PTGDR-2 receptor internalization is monitored by flow cytometry. The $K_b$ is determined using the Schild equation.

Mono- or Combination Treatment

Since both PTGDRs can synergize, antagonizing both PTGDR-1 and PTGDR-2 is an advantageous therapeutic modality for treating and/or preventing lupus. Furthermore, this should avoid any risk of potentiation of $PGD_2$ effect on basophils and other cells via the unblocked PTGDR, if only one of the two $PGD_2$ receptors is targeted.

According to an embodiment, said PTGDR-1 (or PTGDR-2 antagonist) is a dual PTGDR-1/PTGDR-2 antagonist.

According to another embodiment, said PTGDR-1 antagonist is not a dual PTGDR-1/PTGDR-2 antagonist. In said embodiment, the PTGDR-1 antagonist is used either as the sole active ingredient (mono-treatment) for the prevention and/or treatment of SLE, or in combination with at least a PTGDR-2 antagonist (which is neither a dual PTGDR-1/PTGDR-2 antagonist) for the prevention and/or treatment of SLE.

According to another embodiment, said PTGDR-2 antagonist is not a dual PTGDR-1/PTGDR-2 antagonist. In said embodiment, the PTGDR-2 antagonist is used either as the sole active ingredient (mono-treatment) for the prevention and/or treatment of SLE, or in combination with at least a PTGDR-1 antagonist (which is neither a dual PTGDR-1/PTGDR-2 antagonist) for the prevention and/or treatment of SLE.

Additionally, in an embodiment, the PTGDR-1 antagonist, the PTGDR-2 antagonist, or the combination of PTGDR-1 antagonist and PTGDR-2 antagonist, is used in combination with any other standard therapy for the treatment of lupus. Therapeutics useful for the treatment of lupus include, but are not limited to, nonsteroidal anti-inflammatory drugs (NSAIDs), hydroxychloroquine, corticosteroids, cyclophosphamide, azthioprine, methotrexate, mycophenolate mofetil (MMF) (CelleCept®), belimumab, dehydroepiandrosterone, and rituximab.

The PTGDR-1 and/or PTGDR-2 antagonist(s), and optionally further the standard therapeutic for the treatment of lupus, are formulated into one or more pharmaceutical composition(s) comprising said PTGDR-1 and/or PTGDR-2 antagonist(s), and optionally further the standard therapeutic for the treatment of lupus, and at least one carrier, excipient or diluent.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier, excipient or diluent refers to a non-toxic solid, semi-solid or liquid filler, diluent, encapsulating material or formulation auxiliary of any type.

Pharmaceutically acceptable carriers and excipient that may be used in the compositions of this invention include, but are not limited to, ion exchangers, alumina, aluminium stearate, lecithin, self-emulsifying drug delivery systems (SEDDS) such as d-a-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

As appreciated by skilled artisans, the pharmaceutical composition is suitably formulated to be compatible with the intended route of administration. Examples of suitable routes of administration include topical route, oral route, intranasal route, intraocular route, parenteral route, including for instance intramuscular, subcutaneous, intravenous, intraperitoneal or local injections. The oral route can be used, provided that the composition is in a form suitable for oral administration, able to protect the active principle from the gastric and intestinal enzymes.

Preferably, the pharmaceutical composition contains carriers that are pharmaceutically acceptable for an injectable formulation. They may in particular be sterile, isotonic, saline solutions (monosodium phosphate, disodium phosphate, sodium chloride, potassium chloride, calcium chloride or magnesium chloride etc., or mixtures of such salts), or dry, in particular lyophilized, compositions which by means of the addition, as appropriate, of sterilized water or physiological saline, can form injectable solutes.

For combined therapy, (i) the PTGDR-1 antagonist and PTGDR-2 antagonist, (ii) the PTGDR-1 antagonist and the standard therapeutic for the treatment of lupus, (iii) the PTGDR-2 antagonist and the standard therapeutic for the treatment of lupus, or (iv) the PTGDR-1 antagonist, PTGDR-2 antagonist and the standard therapeutic for the treatment of lupus, are formulated in a single pharmaceutical composition, or said PTGDR-1 antagonist, PTGDR-2 antagonist, and standard therapeutic for the treatment of lupus, are formulated in separate pharmaceutical compositions for simultaneous use, separate use, or use spread over time.

Thus the invention also provides for a pharmaceutical composition comprising a PTGDR-1 antagonist and a PTGDR-2 antagonist; or a dual PTGDR-1/PTGDR-2 antagonist; a PTGDR-1 antagonist and a standard therapeutic for the treatment of lupus; a PTGDR-2 antagonist and a standard therapeutic for the treatment of lupus; a PTGDR-1 antagonist, a PTGDR-2 antagonist, and a standard therapeutic for the treatment of lupus; or a dual PTGDR-1/PTGDR-2 antagonist and a standard therapeutic for the treatment of lupus, for use in a method for preventing and/or treating SLE.

Accordingly, it is provided a method for preventing and/or treating SLE in a patient in need thereof, wherein said method comprises administering said patient with a PTGDR-1 antagonist and a PTGDR-2 antagonist, or a dual PTGDR-1/PTGDR-2 antagonist. In an embodiment of said method a standard therapeutic for the treatment of lupus is further step administered with the PTGDR-1 antagonist and PTGDR-2 antagonist, or with the dual PTGDR-1/PTGDR-2 antagonist. A method for preventing and/or treating SLE in a patient in need thereof, wherein said method comprises administering said patient with a PTGDR-1 antagonist or a PTGDR-2 antagonist, and with a standard therapeutic for the treatment of lupus, also makes part of the invention.

The invention also relates to PTGDR-1 antagonist and a PTGDR-2 antagonist; or a dual PTGDR-1/PTGDR-2 antagonist; a PTGDR-1 antagonist and a standard therapeutic for the treatment of lupus; a PTGDR-2 antagonist and a standard therapeutic for the treatment of lupus; a PTGDR-1 antagonist, a PTGDR-2 antagonist, and a standard therapeutic for the treatment of lupus; or a dual PTGDR-1/PTGDR-2 antagonist and a standard therapeutic for the treatment of lupus, for use as a combined preparation for simultaneous use, separate use, or use spread over time, in a method for preventing and/or treating SLE.

The methods of preventing and/or treating SLE according to the invention preferably use an effective amount of PTGDR-1 and/or PTGDR-2 antagonist and/or standard therapeutic for the treatment of lupus.

The expression "effective amount" is intended to mean an amount sufficient to prevent and/or treat a given disease. It will be appreciated that this amount will vary with the effectiveness of therapeutic agent(s) employed, with the nature of any carrier used, with the seriousness of the disease and the age of the patient. The determination of appropriate amounts for any given composition is within the skill in the art, through standard series of tests designed to assess appropriate therapeutic levels.

According to invention the PTGDR-1 antagonist and/or PTGDR-2 antagonist prevent(s) basophil homing to secondary lymphoid organs.

In the frame of the invention, the PTGDR-1 antagonist and/or PTGDR-2 antagonist prevents, limits the extent or reduces the increase in autoantibody titers and/or the occurrence of SLE flares. Alternatively or furthermore, the PTGDR-1 antagonist and/or PTGDR-2 antagonist also prevents, limits the extent or reduces the occurrence organ damages, in particular to kidneys, heart, lungs, and brain. In an embodiment, the PTGDR-1 antagonist and/or PTGDR-2 antagonist prevents, limits the extent or reduces the occurrence of lupus nephritis.

The invention will be further illustrated in view of the following figures and examples.

FIGURES

FIG. 1. Human blood basophil gating strategy and activation status in function of SLE disease activity.

(a) Flow cytometric analysis of CD203c levels on blood basophils from subjects with inactive, mild or active SLE (n=60/40/82, respectively) compared to controls (CT, n=100). (b) Flow cytometric analysis of CD62L levels on blood basophils from subjects with inactive, mild or active SLE (n=43/33/66, respectively) compared to controls (CT, n=90). (c) Flow cytometric analysis of CD63 levels on blood basophils from subjects with inactive, mild or active SLE (n=14/6/12, respectively) compared to controls (CT, n=12). (a-c) Data are normalized to controls' mean and expressed in arbitrary units as means+s.e.m. Statistical analyses were by Mann-Whitney tests. NS: not significant, *: $P<0.05$, : $P<0.01$, *: $P<0.001$.

Figure 2:
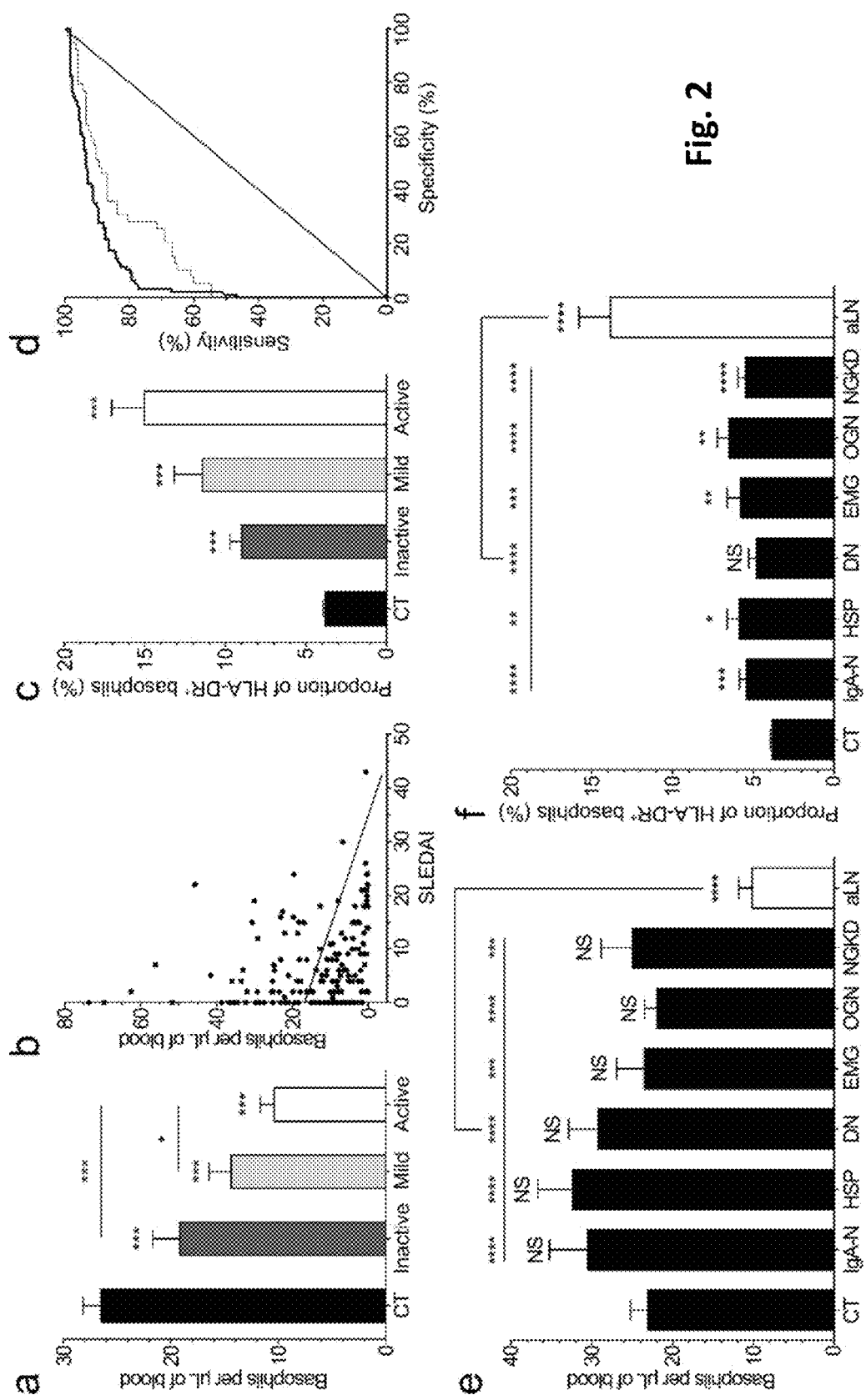

FIG. 2. Basopenia and basophil activation status correlate with disease activity and are specific for lupus nephritis among other active renal diseases.

(a) Blood basophils per μL as determined by flow cytometry from healthy controls (CT) and subjects with inactive, mild or active SLE (n=87/58/38/84, respectively) ad defined in the online methods. (b) Spearman correlation between blood basophil numbers and SLEDAI ($r=-0.3629$, $p<0.0001$) shown on a linear scale. (c) Proportion of blood HLA-DR$^+$ basophils as determined by flow cytometry healthy controls (CT) and subjects with inactive, mild or active SLE (n=96/60/40/84, respectively). (d) Receiver-Operating Characteristic (ROC) analysis of the proportion of HLA-DR+ basophils in SLE patients (n=184) versus controls (n=97) (thick line, AUC=0.9091) and of dsDNA-specific IgG titers in SLE patients (n=123) versus controls (n=39) (dotted line, AUC=0.8384). (e) Blood basophils per μL as in (a) from subjects with the following active renal diseases: IgA-N: IgA nephropathy; HSP: Henoch-Schönlein purpura nephropathy; DN: Diabetic Nephropathy; MN: membranous nephropathy; OGN: Other glomerular nephropathies; NGKD: Non-Glomerular Kidney Diseases; aLN: active Lupus Nephritis; compared to healthy controls (n=40/20/39/22/42/46/81/87, respectively). (f) Proportion of blood HLA-DR+ basophils in patients with active renal diseases as in (e) (n=40/20/39/21/51/47/77, respectively) compared to controls (n=96). (a,c,e,f) Data are expressed as means+s.e.m. Statistical analyses were by Mann-Whitney tests. Comparison to healthy controls' median is shown above each bar and to the corresponding bars when indicated. NS: not significant, *: P<0.05, : P<0.01, *: P<0.001, ****: P<0.0001.

Figure 3:
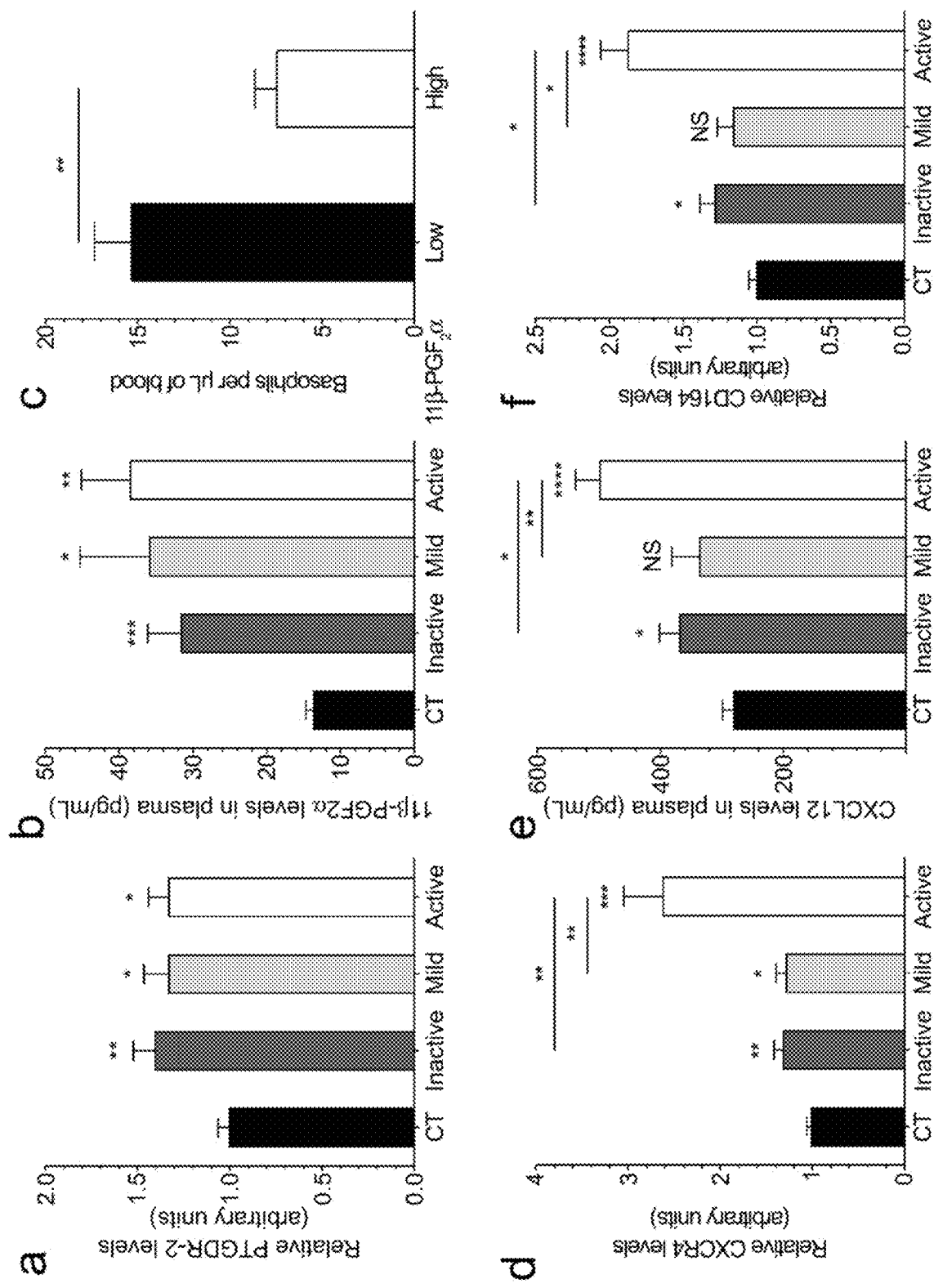

FIG. 3. PGD$_2$/PTGDRs and CXCL12/CXCR4 axes contribute to SLE patient specific basophil phenotype (a) Flow cytometric analysis of PTGDR-2 (CRTH2) levels on blood basophils from healthy controls (CT) and subjects with inactive, mild or active SLE (n=71/48/31/60, respectively). (b) 11β-prostaglandin F$_2$α (11β-PGF2α) levels in plasma from controls and individuals with inactive, mild or active SLE (n=29/31/19/37, respectively) as measured by EIA. (c) Blood basophils per μl of blood in subjects with SLE classified on the basis of low (n=51) or high (n=34) 11β-PGF2α plasma levels (titer below or above CT titer mean+2 standard deviations, respectively). (d) Flow cytometric analysis of CXCR4 levels on blood basophils from CT and subjects with inactive, mild or active SLE (n=66/32/20/51, respectively). (e) CXCL12 levels in plasma from controls and individuals with inactive, mild or active SLE (n=63/43/29/59, respectively) as measured by ELISA. (f) Flow cytometric analysis of the levels of CD164 on blood basophils from CT and subjects with inactive, mild or active SLE (n=33/15/7/26, respectively). (a,d,f) Data are normalized to the mean of CT values and expressed in arbitrary units. (a-f), Statistical analyses were by Mann-Whitney tests. Comparison to healthy controls' median is shown above each bar and to the corresponding bars when indicated. Data are expressed as means+s.e.m. NS: not significant, *: P<0.05, : P<0.01, *: P<0.001, ****: P<0.0001.

Figure 4:
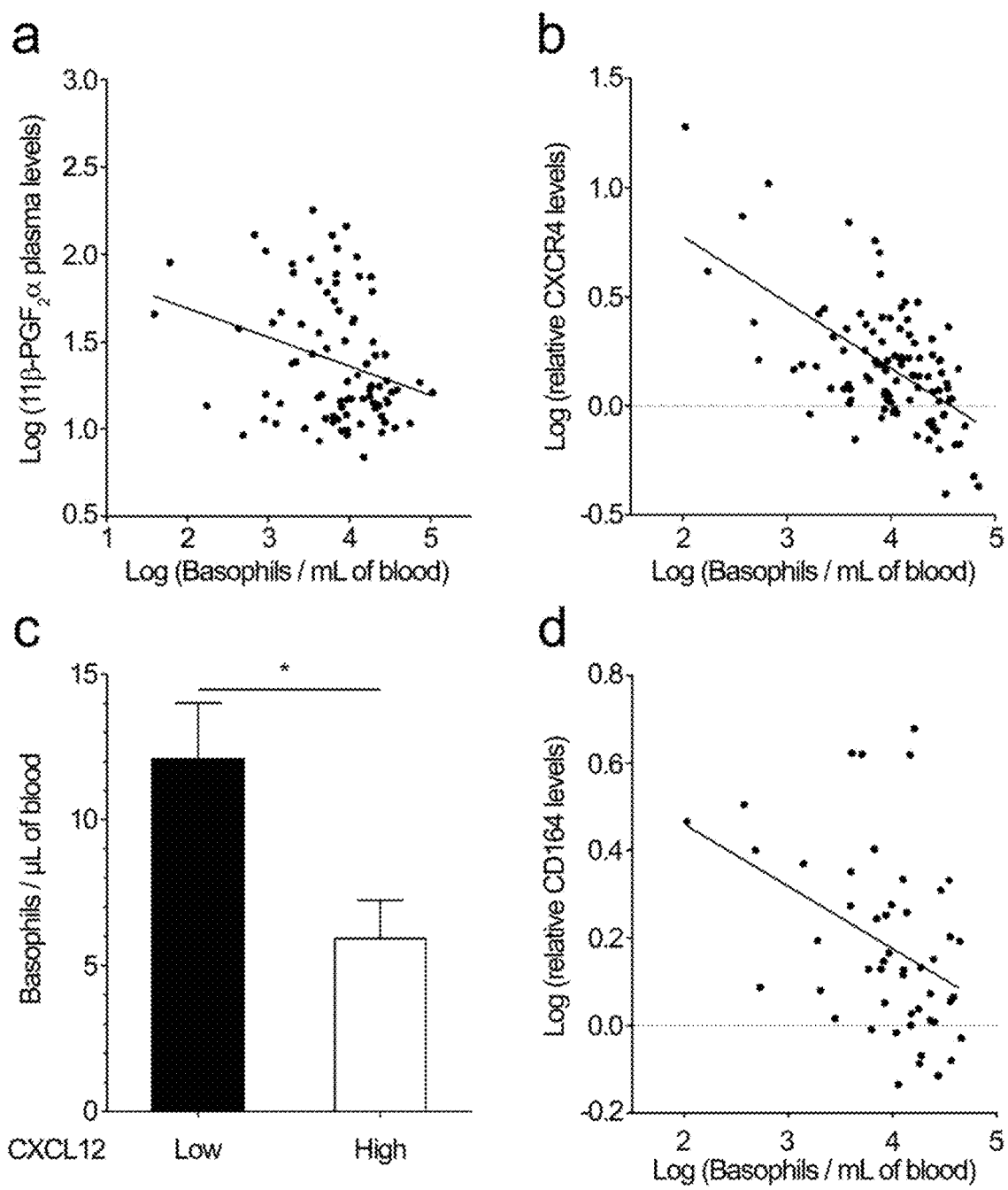

FIG. 4. Associations between plasma 11β-PGF2α & CXCL12 titers, basophil CXCR4 & CD164 expression levels and lupus specific basopenia (a) Spearman correlation between blood basophil number per mL of blood and 11β-PGF2α plasma levels (r=−0.2585, P=0.0169, n=85) shown on a logarithmic scale. (b) Spearman correlation between blood basophil number per mL of blood and relative CXCR4 levels on basophils (as defined in FIG. 2d) (r=−0.4692, P<0.0001, n=101) shown on a logarithmic scale. (c) Blood basophils per μl of blood in subjects with active SLE classified on the basis of low or high CXCL12 plasma levels (titer below or above control titer mean+2 standard deviations, respectively). Data are expressed as means+s.e.m. Statistical analysis was by Mann-Whitney test. *: P<0.05. (d) Spearman correlation between blood basophil number per mL of blood and relative CD164 levels on basophils (as defined in FIG. 2f) (r=−0.4165, P=0.0029, n=49) shown on a logarithmic scale.

Figure 5:
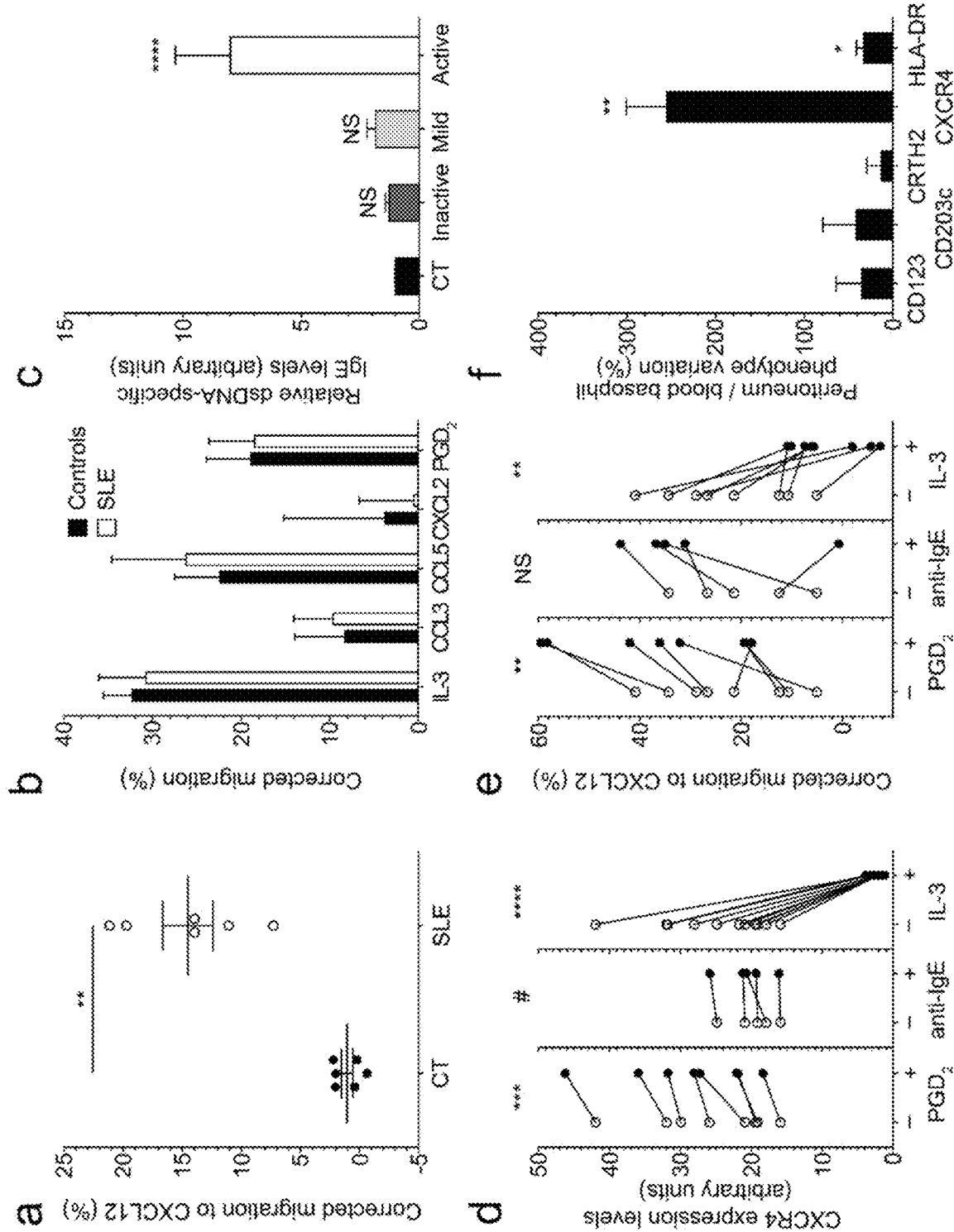

FIG. 5. CXCR4-mediated basophil migration ex vivo and in vivo is enhanced by PGD$_2$ (a) Migration assays of human blood basophils from healthy controls (CT, n=6) and SLE patients (n=6) towards a CXCL12 gradient. (b) Migration assays of human blood basophils towards IL-3, CCL3, CCL5, CXCL2 and PGD$_2$ gradients from healthy controls (Controls, n=8/4/3/4/7, respectively) and from SLE patients (SLE, n=6/3/6/3/5, respectively). (c) Relative dsDNA-specific IgE levels in plasma from inactive, mild or active SLE individuals (n=41/29/51, respectively) normalized to the control values mean (n=38) as measured by ELISA. (a-c) Statistical analyses were by Mann-Whitney tests compared to CT. (d) CXCR4 expression levels on blood basophils after 18 hours of incubation without (−) or with (+) PGD$_2$, mouse anti-human IgE or IL-3 was assessed by flow cytometry. (e) Migration assays of human blood basophils stimulated as in (d) towards a CXCL12 gradient. (d,e) Statistical analyses were by paired Student t test. (f) Expression level variation of the indicated basophil markers between peritoneal and blood basophils from patients undergoing peritoneal dialysis and being treated for non-sterile peritonitis (n=6) were assessed by flow cytometry. Statistical analysis was by one sample t test compared to a 0 theoretical value. (a,b,e) Corrected migration as described in the methods. (a-f) Data are expressed as means±s.e.m. NS: not significant, #: P=0.06, *: P<0.05, : P<0.01, *: P<0.001, ****: P<0.0001.

Figure 6:
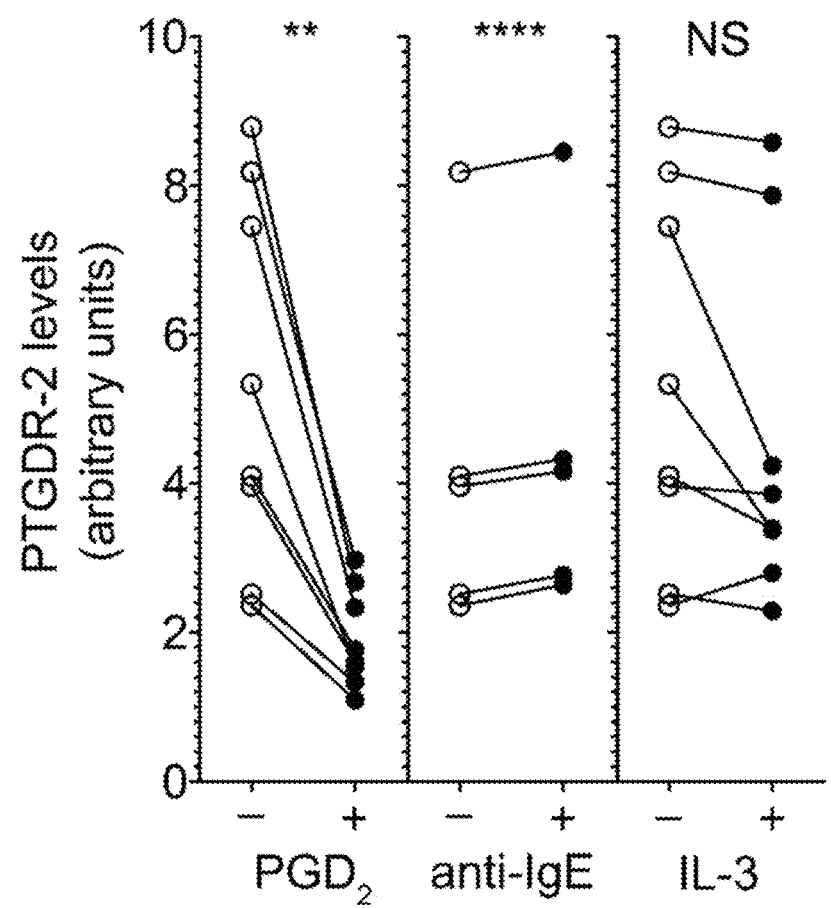

FIG. 6. Suboptimal IgE-mediated basophil activation leads to increased PTGDR-2 expression on human basophils.

PTGDR-2 (CRTH2) expression levels (as defined in online methods) on blood basophils from healthy donors after 18 hours of incubation without (−) or with (+) PGD$_2$, mouse anti-human IgE or IL-3. Statistical analyses were by paired Student t test.

Figure 7:
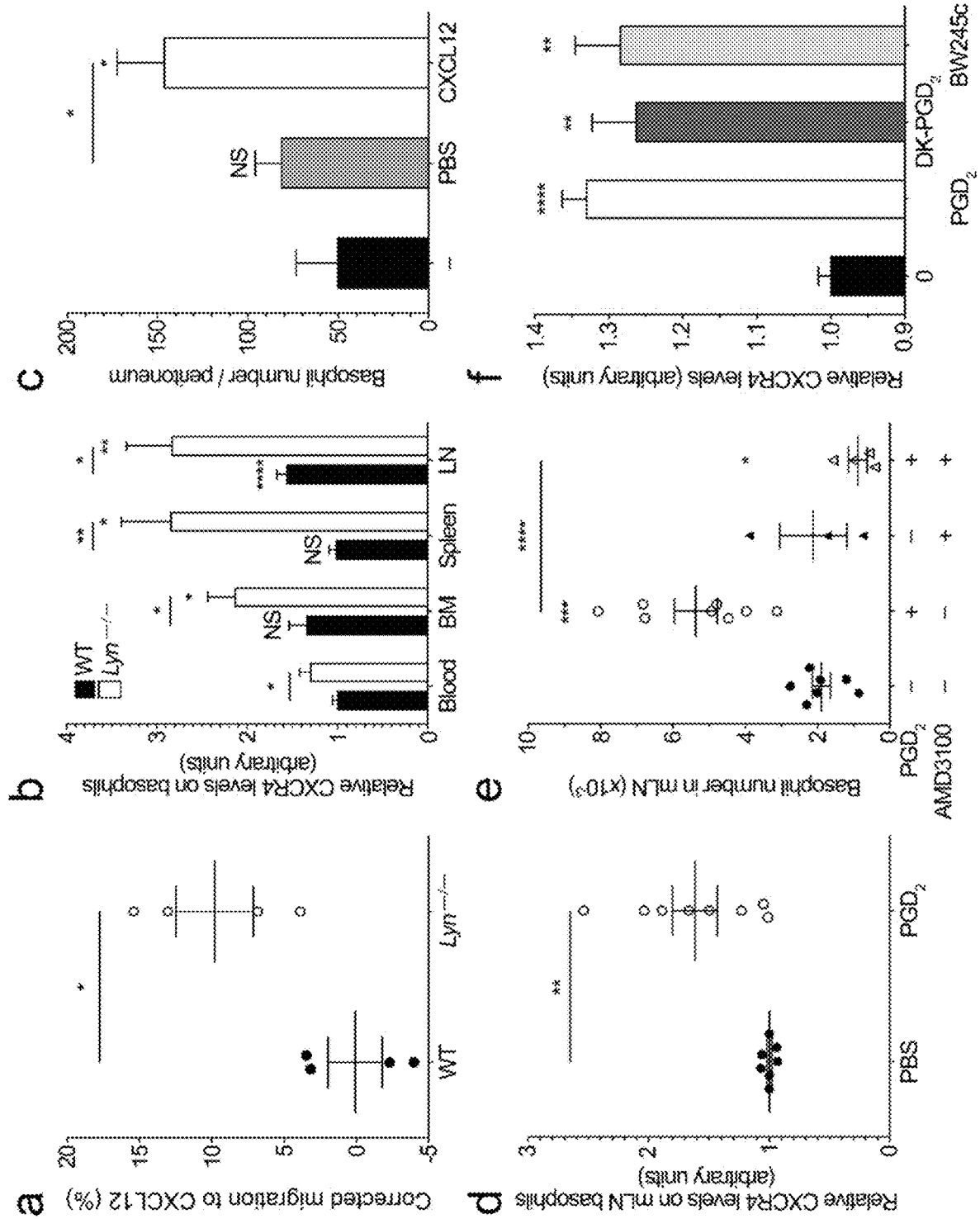

FIG. 7. PGD$_2$ is sufficient to enhance the CXCL12-dependent basophil homing to SLOs occurring in lupus-prone mice (a) Ex vivo migration of basophils from whole WT or Lyn$^{-/-}$ splenocytes to CXCL12. (b) CXCR4 expression levels on basophils from the indicated compartments in aged WT (n=16) and Lyn$^{-/-}$ (n=14) animals. Data are normalized to the mean CXCR4 expression level of WT blood basophils. Statistical analyses placed directly above each bar compared the value for one given compartment to the blood compartment of the corresponding genotype. Statistical analyses between both genotypes for each compartment are also indicated. (c) Basophil number per peritoneum in young WT mice 24 hours after intraperitoneal (ip) injection of PBS or CXCL12 and compared to steady state (−) values (n=13/15/5, respectively). (d) CXCR4 expression levels on basophils from mesenteric lymph nodes (mLN) of young Lyn$^{-/-}$ mice 24 hours after PBS or PGD$_2$ ip injection normalized to PBS injected mice values' mean. (e) Basophil number in mLN of young Lyn$^{-/-}$ mice 24 hours after ip injection of the indicated compound(s). (f) CXCR4 expression levels on spleen basophils from 15 weeks old WT mice incubated ex vivo for 24 hours with the indicated compound and normalized to the control values' mean. (a-f) Data are expressed as means±s.e.m. Basophils number and CXCR4 expression were assessed by flow cytometry. Statistical analyses were by unpaired t test with Welch's correction (a-e) and by paired Student t test (f). NS: not significant, #: P=0.058, *: P<0.05, : P<0.01, *: P<0.001, ****: P<0.0001.

Figure 8:
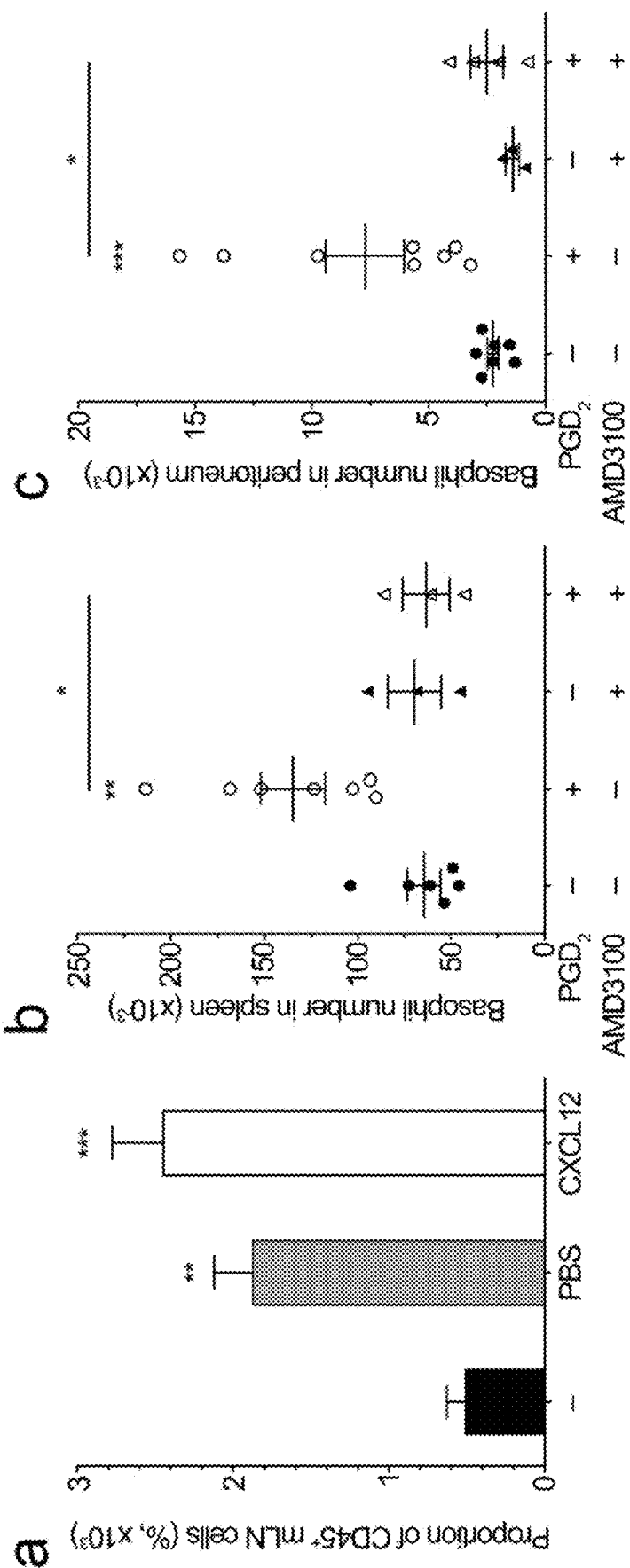

FIG. 8. CXCL12 or PGD$_2$ ip injection in mice induce a CXCR4-dependent basophil accumulation in SLOs and peritoneum.

(a) Proportion of basophil (×103) among living CD45+ cells in mesenteric lymph node (mLN) of young WT mice 24 hours after intraperitoneal (ip) injection of PBS (n=13) or CXCL12 (n=15) and compared to steady state (−) values (n=5). (b) Basophil number in spleen of young Lyn$^{-/-}$ mice 24 hours after ip injection of the indicated compound(s). (c) Basophil number in peritoneum of Lyn$^{-/-}$ mice 24 hours after ip injection of the indicated compound(s). Data are expressed as means±s.e.m. Statistical analyses were by unpaired Student t test with Welch's correction. NS: not significant, *: P<0.05, : P<0.01, *: P<0.001.

Figure 9:
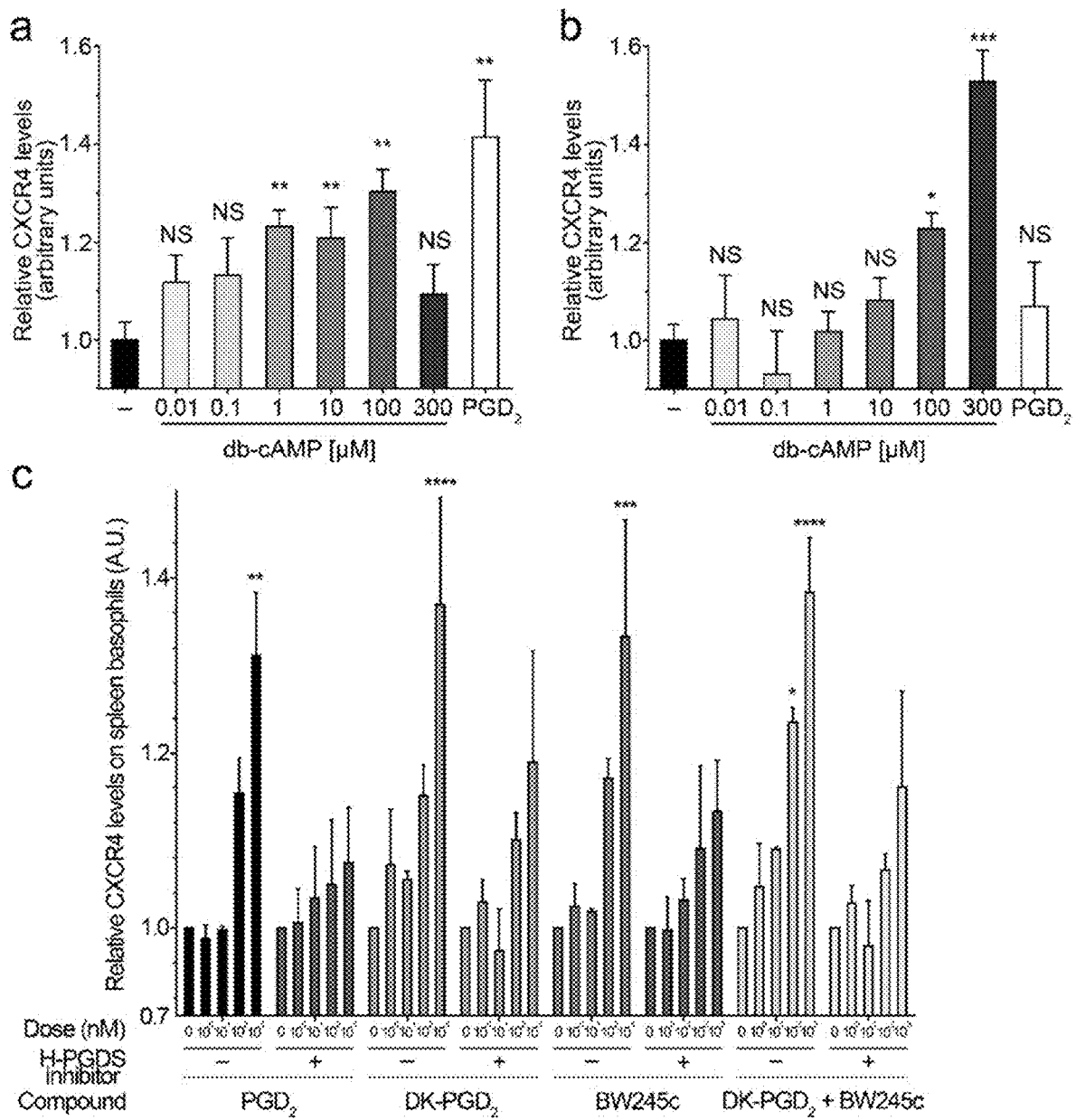

FIG. 9: cAMP and PTGDRs specific agonist effects on CXCR4 expression by mouse spleen basophils ex vivo.

(a-b) Relative CXCR4 expression levels on basophils (defined as CD19$^-$TCRβ$^-$CD3$^-$CD49b$_+$FcεRIα$^+$CD123$^+$) CD45$^{lo}$ and T cells (defined as CD45$^+$CD3$^+$TCRβ$^+$ cells) in splenocytes incubated 4 hours without (−) or with the indicated concentration of N6,2'-O-dibutyryl-adenosine 3':5'-cyclic monophosphate (db-cAMP) or 1 μM PGD$_2$ as determined by flow cytometry. Statistical analyses were by paired Student t tests. NS: not significant, *: P<0.05, : P<0.01, *: P<0.001. (c) Relative CXCR4 expression levels on spleen basophils (defined as in (a)) incubated 4 hours without (0) or with the indicated concentration (nM) of the indicated compound(s). DK-PGD$_2$: 13,14-dihydro-15-keto-PGD$_2$ (PTGDR-2 specific agonist); BW245c: 3-(3-Cyclohexyl-3-hydroxypropyl)-2,5-dioxo-(R*,S*)-(±)-4-imidazolineheptanioc acid (PTGDR-1 specific agonist) as determined by flow cytometry. Statistical analysis was by two-ways ANOVA followed by a Tukey's multiple comparisons test. (a-c) Data are normalized to control value mean (per group, n=4 to 8). Data are expressed as mean+s.e.m. All experiments were realized with splenocytes from 8-12 weeks old WT mice.

Figure 10:
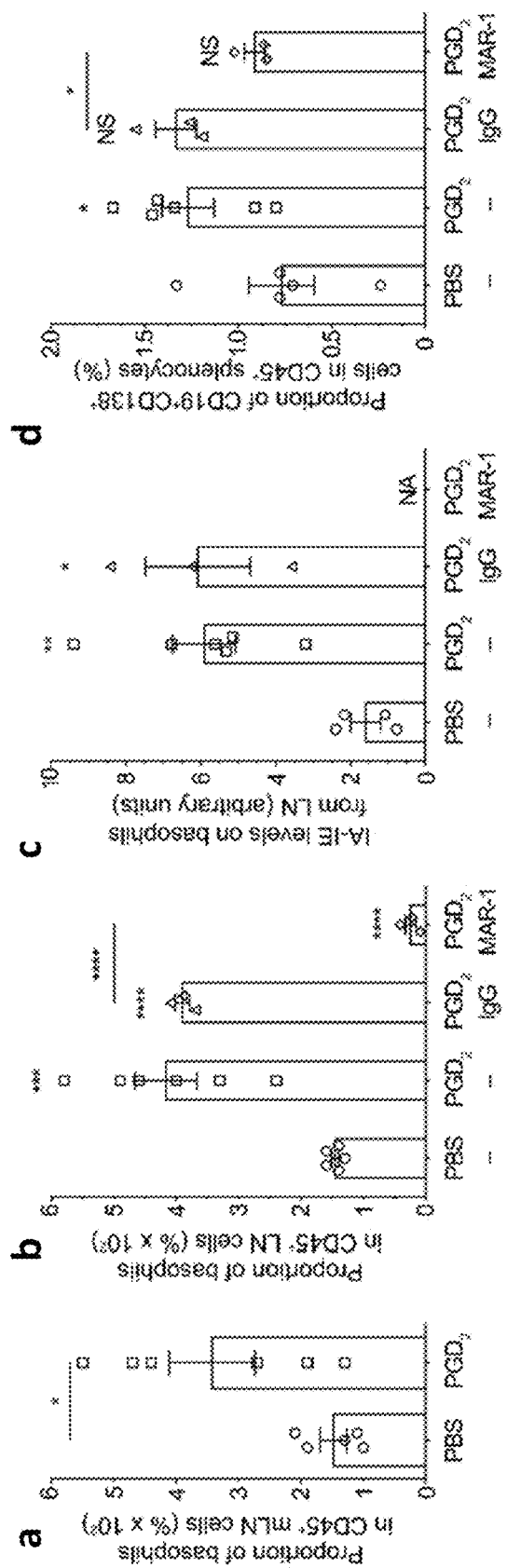
Figure 10:
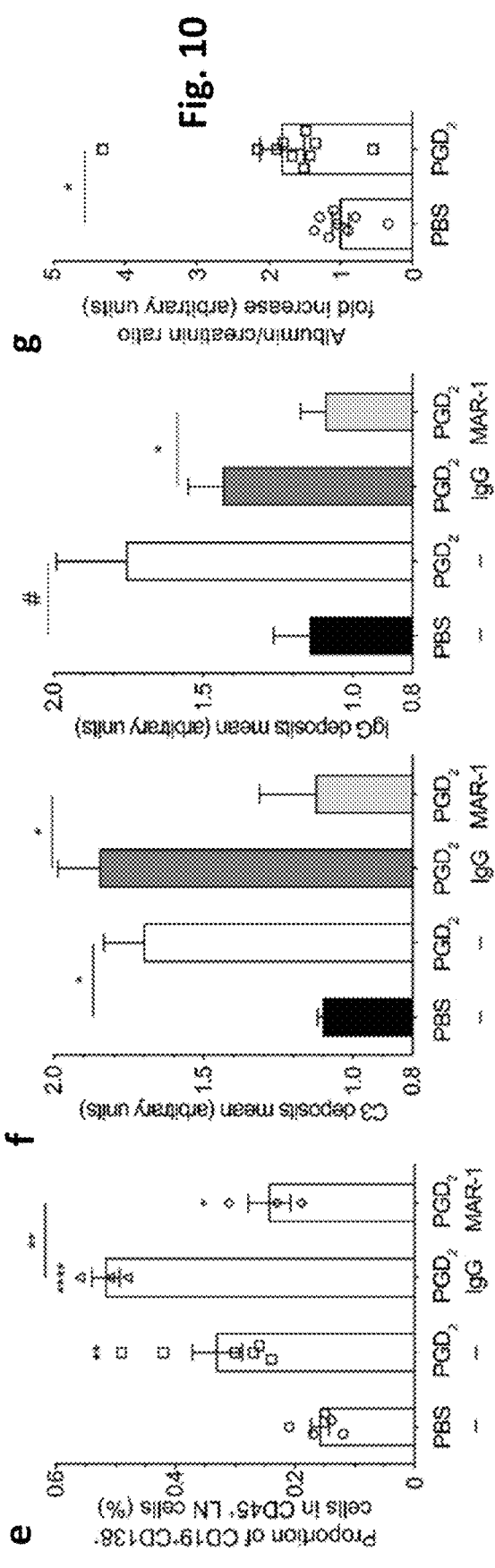

FIG. 10. Blockade of basophil accumulation in SLOs dampens lupus-like disease activity (a,b) Proportion of basophils (CD19$^-$TCRβ$^-$CD49b$^+$ FcεRIα$^+$CD123$^+$)CD45$^{lo}$) among singlets living CD45$^+$ cells in mesenteric (a) and other (cervical, brachial and inguinal) lymph nodes (b) from 10 to 12 weeks-old Lyn$^{-/-}$ mice injected over ten days with PBS (open circles) or PGD$_2$ alone (open squares), and PGD$_2$ injected and basophil depleted (MAR-1) (open diamonds) or not (IgG) (open triangles) as described in the methods. (c) IA-IE expression levels on LN basophils from mice as in (b). NA: not applicable. (d,e) Proportion of short lived plasma cells CD19$^+$CD138$^+$ among singlets living CD45$^+$ cells in spleen (d) and lymph nodes (e) in the same mice as in (b). (f) Representative immunofluorescence staining for C3 and IgG deposits in kidneys from mice as indicated in (b) (scale bar=1 mm) and their corresponding quantifications in PBS (n=3), PGD$_2$ (n=4), PGD$_2$+control IgG (n=3) and PGD$_2$+MAR-1 (n=3) injected mice. (g) Fold increase in urine albumin/creatinine ratio before and after PBS or PGD$_2$ 10 days-long treatment. (a-e) Basophil, plasma cell numbers and IA-IE expression levels were assessed by flow cytometry. (a-g) Data are expressed as means±s.e.m. Statistical analyses were by unpaired student t tests. #: P=0.0571, *: P<0.05, : P<0.01, *: P<0.001, ****: P<0.0001. One representative out of three independent experiments is shown.

Figure 11:
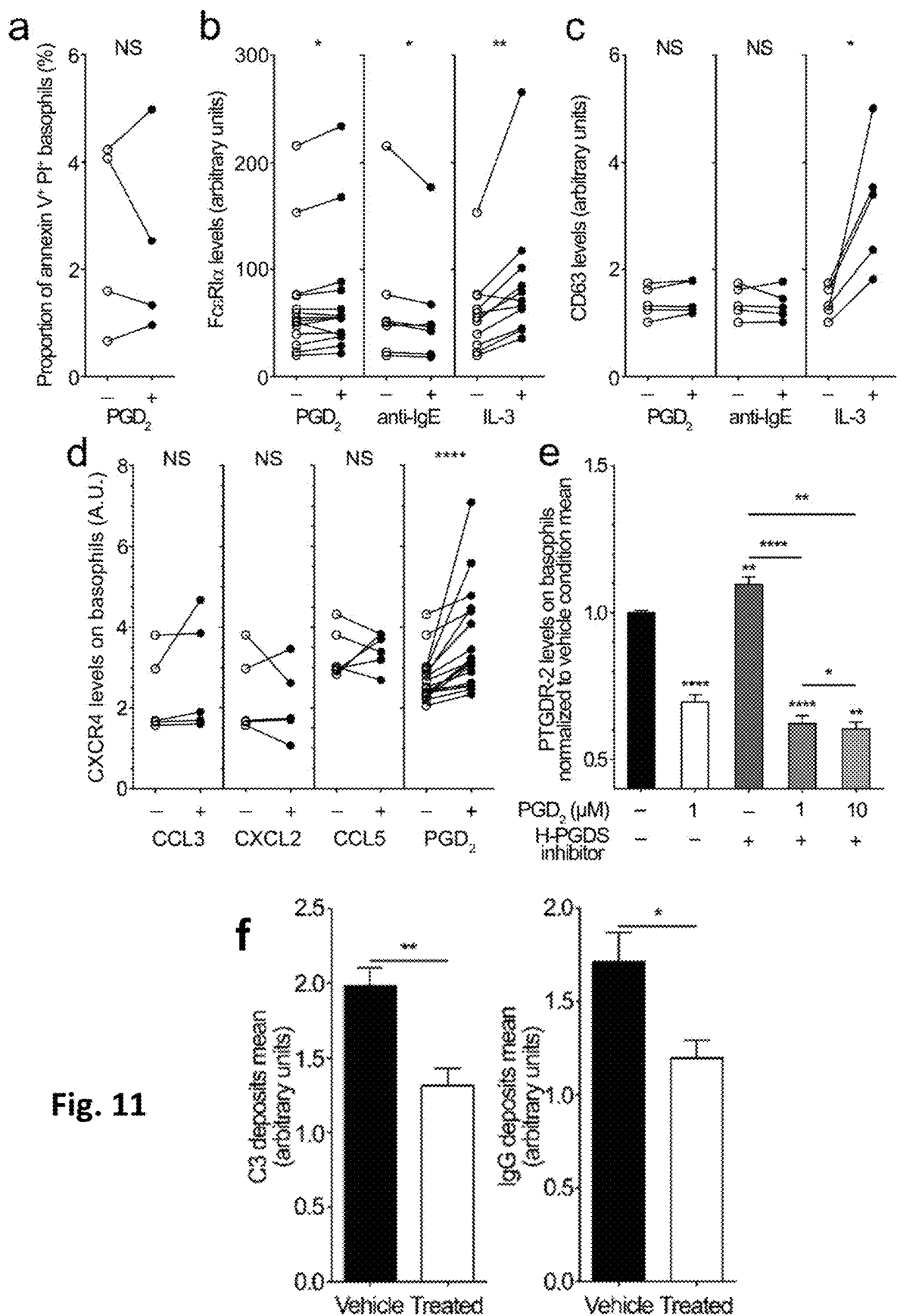

FIG. 11. Blockade of basophil accumulation in SLOs dampens lupus-like disease activity Quantifications of immunofluorescence staining for C3 and IgG deposits in kidneys from aged Lyn$^{-/-}$ mice treated (n=8) or not (vehicle, n=9) with PTGDR-1 and PTGDR-2 antagonists for ten days.

Figure 12:
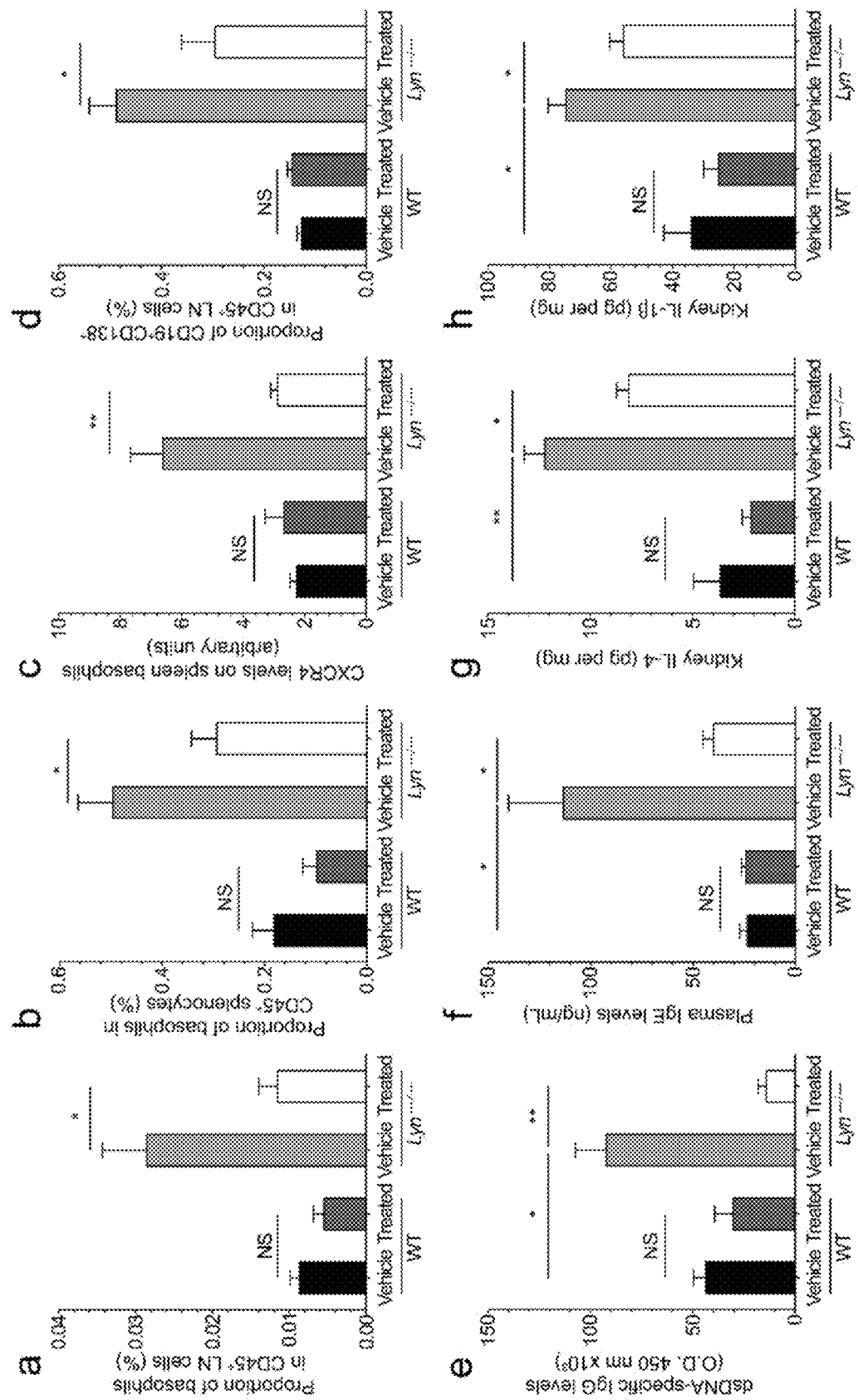

FIG. 12. Targeting PTGDRs blocks CXCR4-mediated basophil accumulation in SLOs and reduces the lupus-like disease activity.

(a-h) Comparisons between aged wild-type (WT) and Lyn$^{-/-}$ mice treated or not (vehicle) for 10 days with PTGDR-1 and PTGDR-2 antagonists as described in the online methods. (a,b,c) Flow cytometric analysis of basophils among living CD45$^+$ cells in lymph nodes (cervical, axillar, inguinal and mesenteric) (a) and spleen (b). (c) CXCR4 expression levels on spleen basophils. (d) Proportion of short lived plasma cells CD19$^+$CD138$^+$ among living CD45$^+$ cells in lymph nodes as in (a) was determined by flow cytometry. (e) Optical density (O.D.) values at 450 nm of dsDNA-specific IgG in plasma from the indicated mice as measured by ELISA (×10$^3$). (f) Total IgE levels as measured by ELISA in plasma from the indicated mice. (g,h) IL-4 (g) and IL-1β (h) concentration in pg per mg of total kidney protein extract from the indicated mice as measured by ELISA. (a-h) WT vehicle, n=5; WT treated, n=4; Lyn$^{-/-}$ vehicle, n=8; Lyn$^{-/-}$ treated, n=8. Data are expressed as mean+s.e.m. Statistical analyses were by unpaired Student t tests. NS: not significant, *: P<0.05, **: P<0.01.

Figure 13:
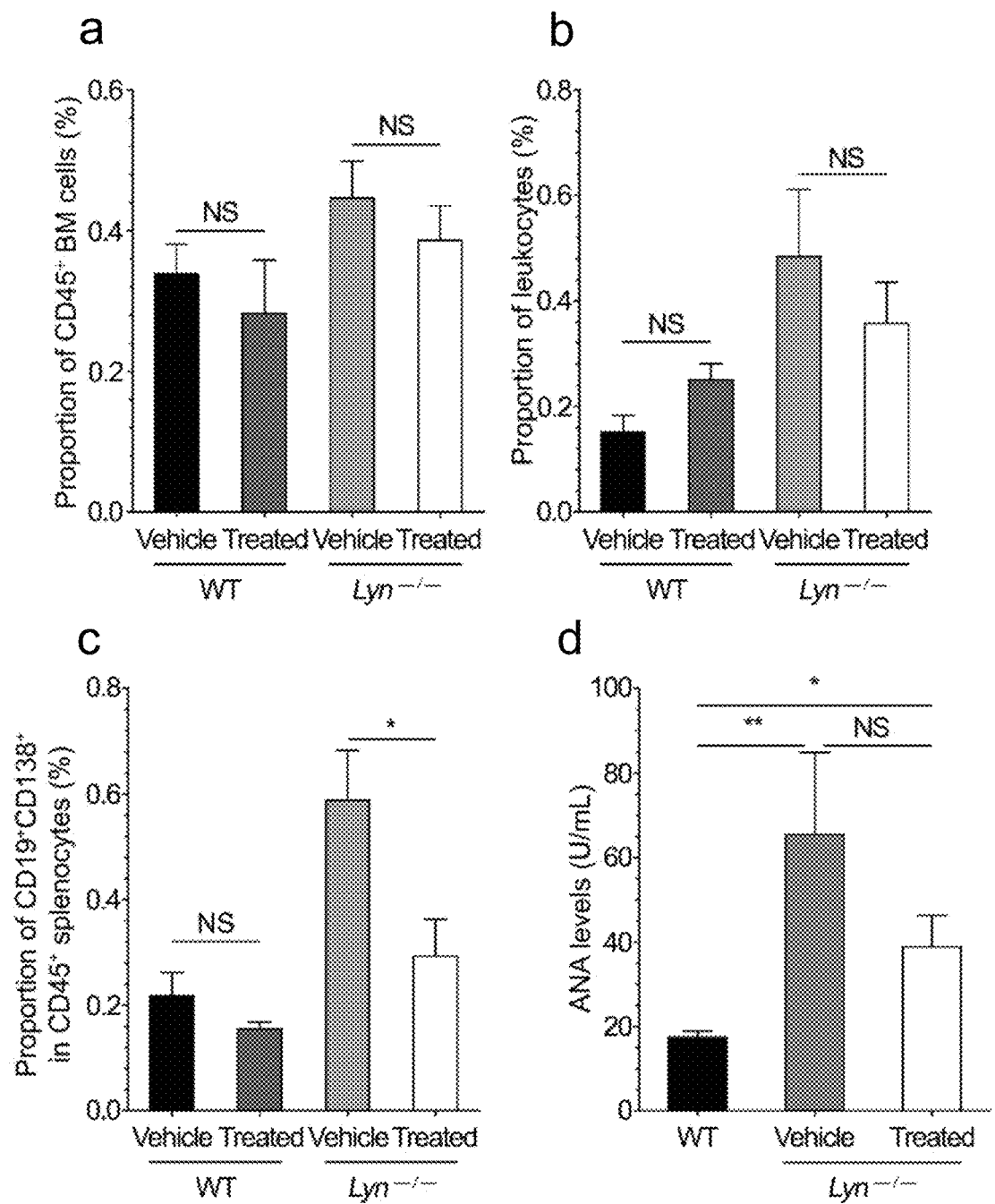

FIG. 13. Treatment with PTGDRs antagonists reduces specifically basophil accumulation in SLOs leading to reduced short-lived plasma cell number and serum ANA titers.

(a-d) Comparisons between aged wild-type (WT) and Lyn$^{-/-}$ mice treated or not (vehicle) with PTGDR-1 and PTGDR-2 antagonists for ten days. (a,b) Flow cytometric analysis of basophil proportion among CD45+ bone marrow (BM) cells (a) and blood leukocytes (b). (c) Flow cytometric analysis of short lived plasma cells CD19+CD138+ among living CD45+ cells. (d) Anti-nuclear antibodies (ANA) levels as measured by ELISA in plasma from the indicated mice. (a-d) WT vehicle, n=5; WT treated, n=4; Lyn$^{-/-}$ vehicle, n=8; Lyn$^{-/-}$ treated, n=8. Data are expressed as means+s.e.m. (a-c) Statistical analyses were by unpaired Student t test. (d) Statistical analysis was by Mann-Whitney test. NS: not significant, *: P<0.05, **: P<0.01.

Figure 14:
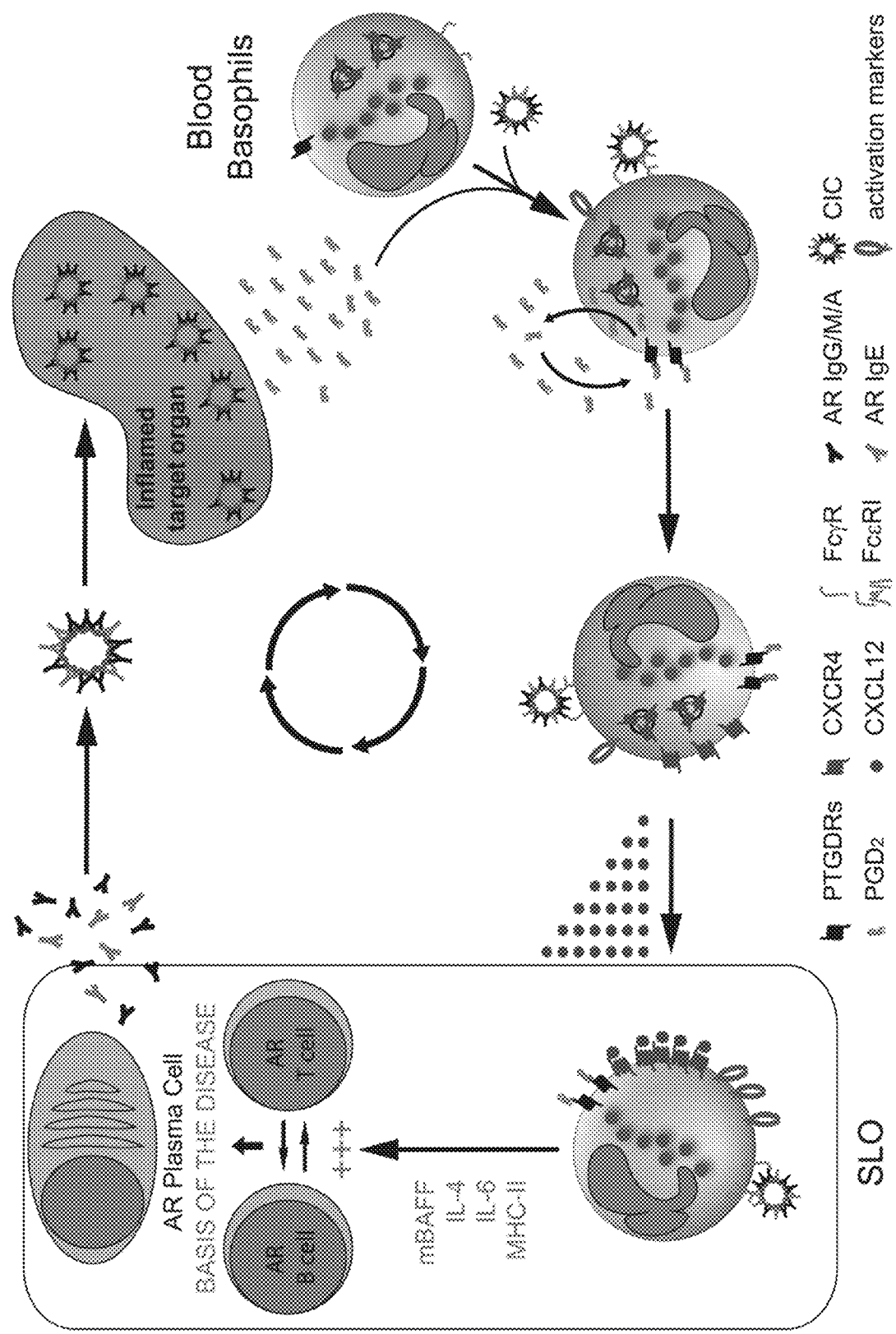

FIG. 14. Graphical abstract

In systemic lupus erythematosus (SLE), a loss of self-tolerance induces the expansion of autoreactive (AR) T and B cells. Autoreactive plasma cells secrete autoreactive antibodies which will bind self-antigens of nuclear origin and complement factors to form circulating immune complexes (CIC). The deposition of these CIC or autoreactive antibodies in target organs is associated with local lesions, inflammation (and PGD$_2$ production), and organ damages. Healthy basophils can get activated by the binding of CIC to Fc receptors (FIERI and FcγRs) to express more prostaglandin D2 (PGD$_2$) receptors (PTGDRs) and activation markers such as CD203c. As chronic inflammation settles, so does the secretion of various inflammatory mediators in blood, including PGD$_2$. PGD$_2$ is sufficient to induce PGD$_2$ production by circulating basophils themselves leading to an autocrine effect of PGD$_2$. This leads to an increased surface expression of CXCR4 and enable basophil sensitivity to CXCL12 gradients. As a result, basophils are more eager to migrate to SLOs, which are known to secrete more CXCL12 during lupus pathogenesis. There, basophils support autoreactive T and B cells through their expression of activating molecules such as mBAFF, MHC-II or the secretion of various cytokines such as IL-4 and IL-6. Moreover, basophils can promote autoreactive antibody production and IgE class switching of B cells. As CIC and autoreactive IgE titers increase, so will targeted organ inflammation, PGD$_2$ and CXCL12 titers and basophils homing to SLOs. It is assumed that basophils drive an amplification loop of the disease and blocking their recruitment to SLOs would prevent rise in autoantibody titers and consequent flares.

EXAMPLES

Example 1: Materials and Methods

Mice.

C57BL/6J wild-type (WT) mice were purchased from Charles River Laboratories (L'Arbresle, France) and Lyn$^{-/-}$ mice on a pure C57BL/6 background were bred in our animal facility. For lupus-like disease studies, mice were aged for a minimum of 40 weeks before treatment and analysis. For other ex vivo or in vivo analysis, young mice were between 8 and 12 weeks old, unless otherwise specified. Mice were maintained in specific pathogen-free conditions, used in accordance with French and European guidelines and approved by local ethical committee and by the Department of Research of the French government under the animal study proposal 02484.01.

Patients.

Blood samples were collected from adult subjects enrolled in a prospective long term study of systemic lupus erythematosus (SLE) and chronic renal diseases. The study was approved by the Comite Regional de Protection des Personnes (CRPP, Paris, France) under the reference ID-RCB 2014-A00809-38. Diagnostics of inpatients were not known by the investigators at the time of sample processing and flow cytometry analysis. SLE samples were obtained from in- and outpatients and clinical data were harvested after approval by the Comission Nationale de l'Informatique et des Libertés (CNIL). All SLE subjects fulfilled the American College of Rheumatology classification criteria for SLE. SLE and healthy control (HC) donor characteristics are shown in Table 1 (below). Lupus activity was assessed by SELENA-SLEDAI (Safety of Estrogens in Lupus Erythematosus National Assessment—SLE Disease Activity Index) scores. Based on the SLEDAI score, lupus activity was classified as inactive (0-1), mild (2-4) and active (>4). All samples were collected in heparin blood collection tubes and processed within 4 hours. A written informed consent was obtained from all subjects. Active lupus nephritis subjects were defined by histologically active classes III or IV+/−V nephritis, in accordance with the ISN/RPS classification (Weening, J. J., et al., J. Am. Soc. Nephrol. 15, 241-250 (2004)).

Antibodies and Flow Cytometry

All antibodies were from commercial sources. Flow cytometry acquisition was done with a LSRII Fortessa using DIVA software (BD Biosciences). Blood sample processing procedure was as previously described (Charles, N. et al., Nat. Med. 16, 701-707 (2010)). All data relative to marker expression levels are expressed as the ratio between the geometric mean fluorescence intensity (Geo MFI) of the indicated marker on the cells of interest and the Geo MFI of the corresponding isotype control. Data were normalized or not as indicated in figure legends. Data analysis was realized with FlowJo v.X.0.7 (Treestar).

Chemokines, Cytokines, 11β-PGF$_{2α}$ and Immunoglobulin Measurement Assays

All commercial assays were performed according to the manufacturer instructions. 11β-Prostaglandin F$_{2α}$ enzyme immunoassay (EIA) kits were from Cayman Chemicals (Ann Arbor, Mich.). Mouse ANA enzyme linked immunosorbent assay (ELISA) kits were from ADI (San Antonio, Tex.). Human and mice CXCL12 ELISA kits were from R&D Systems (Minneapolis, Minn.). Assessment of cytokine content in the kidney was previously described (Charles, N. et al., Nat. Med. 16, 701-707 (2010)). Mouse IL4 and ID1β ELISA kits were from BioLegend (San Diego, Calif.). Mouse IgE Quantification ELISA kits were from Bethyl Laboratories (Montgomery, Tex.). Human and mouse anti-dsDNA IgG and IgE were quantified as previously described (Charles, N. et al., Nat. Med. 16, 701-707 (2010)). Absorbance was assessed by an Infinite 200 Pro plate reader (TECAN, Männedorf, Switzerland).

Human Basophil Purification and Enrichment.

Human basophils were purified to >95% by negative selection with the Human Basophils Enrichment kit (Stemcell Technologies, Grenoble, France) for culture, stimulation and chemotaxis experiments. In some chemotaxis experiments, human basophils were enriched to 3-5% by negative selection with the Human PE positive selection kit (Stemcell Technologies) by using a cocktail of PE-conjugated anti-CD3, CD19 and CD89 (BioLegend). These kits were used following manufacturer instructions.

Imaging Flow Cytometry

Basophils were enriched to 3-5% as described above and frozen at −80° C. in 90% FCS 10% dimethyl sulfoxide until enough samples were collected. Thawed cells were stained, fixed (IC fixation buffer, eBioscience) and permeabilized (Wash Perm Buffer, BioLegend) following the manufacturers' instructions. Anti-human CXCR4 or its isotype (BioLegend) were used for intracellular staining. DAPI was added prior to cytometry analysis. Basophils were gated as Singlets cells/Focus high/DAPI high/PE$^-$ CD123$^+$ FcεRIα$^+$ CD303$^-$. CXCR4 expression was determined for each basophil as the ratio of the geometric mean of their CXCR4 intensity on the mean basophil CXCR4 FMO (Fluorescence Minus One) intensity. Internalization scores were determined using Fc☐RI☐ staining as a membrane marker and CXCR4 staining as the probe. For each sample, externalization score corresponds to [1—internalization score]. All analyses were performed using the ImageStream X Mark II imaging flow cytometer and the IDEAS v6 software (AMNIS).

Basophil Culture and Stimulation

Human basophils and mouse splenocytes were cultured in culture medium (RPMI 1640 with Glutamax and 20 mM HEPES, 1 mM Na-pyruvate, non-essential amino acids 1× (all from Life Technologies, Saint-Aubin, France), 100 µg/ml streptomycin and 100 U/ml penicillin (GE Healthcare, Vélizy, France) and 37.5 µM β-mercaptoethanol (Sigma-Aldrich, MO)) supplemented with 20% heat-inactivated fetal calf serum at 37° C. and 5% CO$_2$. 18 hours-long stimulation prior to migration assays were done in culture medium at 1×10$^6$ cells per mL by adding 1 nM of IL-3 (Peprotech), 1 µM of prostaglandin D2 (PGD$_2$), 1 µM of the PTGDR-1 specific agonist BW245c, 1 µM of the PTGDR-2 specific agonist 13,14-dihydro-15-keto Prostaglandin D$_2$ (DK-PGD$_2$) (all from Cayman chemicals) or 5 ng/mL of anti-IgE (mouse anti-human IgE or rat anti-mouse IgE, both from Thermo Scientific). All cells were washed twice before any migration assay. Control conditions were always with the same vehicle concentration as stimulated conditions.

For CXCR4 overexpression modulation by PTGDRs antagonists, PGD$_2$ and H-PGDS inhibitor, purified basophils were resuspended in RPMI containing 0.1% BSA+/− the following compounds: vehicle (ethanol 0.1‰), 1 µM PTGDR-1 antagonist Laropiprant, 1 µM PTGDR-2 antagonist CAY10471, 1 or 10 µM PGD$_2$, and 1 µM of Prostaglandin D Synthase (hematopoietic-type) Inhibitor I (catalog #16256) (all from Cayman Chemical). Cells were incubated for 4 hours at 37° C. and 5% CO$_2$ and surface expression of the indicated markers were assessed by flow cytometry.

Basophil Migration and Apoptosis Assays

Migration assays were performed in culture medium supplemented with 0.1% bovine serum albumin (BSA, Sigma-Aldrich) in Transwell 5 µm polycarbonate permeable support 6.5 mm inserts (Corning, N.Y., N.Y.) for 3 hours at 37° C. and 5% CO$_2$ with 1×10$^5$ purified basophils or 2×10$^5$ enriched basophils at 1×10⁶ cells per mL. Purified or enriched basophils from the upper and bottom chambers were counted at the end of the assay. Basophil content and phenotype was determined by flow cytometry by analyzing more than 100 basophils. Purification or enrichment of human basophils didn't show any difference in the measured migration for all tested chemokines. Migration was defined as the ratio between the number of basophils in the bottom chamber and the number of basophils in the upper plus the bottom chambers. Spontaneous migration was defined as the migration observed without any chemokine in the bottom chamber. Corrected migration was defined as the difference between specific and spontaneous migration. For migration assays the following concentrations (known to be optimal) were used for each compound: Human IL-3: 300 pM (Peprotech), human CCL3, CCL5, and CXCL12: 50 nM; CXCL2 (all from BioLegend) and $PGD_2$ (Cayman chemicals): 100 nM. Migration to human CCL3, CCL5, CXCL2, and $PGD_2$ was done in the presence of IL-3 at 300 pM in both chambers. Migration with IL-3 represents chemokinetism: IL-3 was added in both chambers to the same concentration and compared to the spontaneous migration observed without IL-3. Effects of 24 hours incubation with IL-3 or PGD2 (as described above) on basophil apoptosis were estimated by using the FITC Annexin V Apoptosis Detection Kit from BD Biosciences and used accordingly to manufacturer's instructions.

In Vivo Experiments

For CXCL12-induced basophil in vivo migration assays, 200 μL of PBS containing 100 ng of murine CXCL12 or PBS alone were injected intraperitoneally (ip) in 8-12 weeks old WT mice. For $PGD_2$-induced basophil in vivo migration assays, 100 μL of PBS (with 2 μL of ethanol) alone, or PBS±20 nmoles of $PGD_2$±200 μg of AMD3100 (all from Cayman Chemicals) were injected ip in 8-12 weeks old $Lyn^{-/-}$ mice. In all cases, 24 hours later, mice were euthanized and peritoneal lavage, blood, mesenteric lymph nodes and spleen were collected and prepared for FACS analysis as previously described (Charles, N. et al., Nat. Med. 16, 701-707 (2010)). For acceleration of disease development by $PGD_2$ injections, 12 weeks old $Lyn^{-/-}$ mice were injected ip with 20 nmoles of $PGD_2$ or vehicle in PBS, every two days for 10 days, for a total of 6 injections. Mice were analyzed the day following the last injection. For treatment with PTGDRs antagonists, aged WT and $Lyn^{-/-}$ mice were treated by oral doses of 5 mg/kg of Laropiprant and CAY10471 (Cayman chemicals) or equivalent dose of ethanol (vehicle) in tap water twice a day for ten days. Then, mice were euthanized and blood, plasma, spleen, bone marrow, kidneys and lymph nodes (cervical, brachial, inguinal and mesenteric) were analyzed as previously described (Charles, N. et al., Nat. Med. 16, 701-707 (2010)). The treatment didn't affect weight and cell numbers in the different organs. Cell viability was assessed by the utilization of Ghost Dye Violet 510 (Tonbo, San Diego, Calif.).

Analysis of Glomerular Deposition of IgG and C3, and Kidney Function.

Kidney preparation for immunofluorescence analysis of C3 and IgG deposits was as previously described (Charles, N et al. Nat. Med., 2010, 16, 701-707, 2159). Quantification of C3 and IgG deposits was realized by using ImageJ software (v1.49p, NIH, USA). A minimum of 20 glomeruli was quantified per kidney. For assessment of kidney function the albumin/creatinine ratio (ACR) was determined. Urine was collected from each mouse before and after treatment. The albumin concentration was measured with a mouse albumin ELISA (Bethyl laboratories, Montgomery, Tex.). A creatinine assay (R&D systems, Minneapolis, Minn.) was used to determine urine creatinine concentrations. Results are expressed as a fold increase corresponding to the ratio of the ACR after/before treatment.

Statistical Analysis.

Distribution was assessed with D'Agostino-Pearson omnibus normality test or Kolmogorov-Smirnov test, depending on sample size, to perform appropriate analyses. When more than 2 groups were compared, one-way analysis of variance (ANOVA) tests were conducted before the indicated post-tests when significance (p<0.05) was reached. All tests run were two-tailed. Statistics were performed with GraphPad Prism V5 and V6 (GraphPad) and with STATA 12 (Statacorp) softwares.

Example 2: Results

Specific SLE and Lupus Nephritis Basophil Phenotype

On a cohort of individuals with SLE (n=188, Table 1), we first validated that SLE subject basophils had an activated phenotype as shown by increased CD203c (a basophil activation marker) and CD62L (L-selectin, involved in leukocyte rolling) expressions as compared to healthy control (HC) ones (n=98, FIG. 1a-b, Table 1) (Charles, N. et al., Nat. Med. 16, 701-707 (2010)).

However, SLE basophils did not display a degranulated phenotype (as measured by their CD63 expression level, FIG. 1c). Basopenia appeared to be a good marker of disease correlating with SLE disease activity index (SLEDAI, American College of Rheumatology Ad Hoc Committee on Systemic Lupus Erythematosus Response, C. The American College of Rheumatology response criteria for systemic lupus erythematosus clinical trials: measures of overall disease activity. Arthritis Rheum. 50, 3418-3426 (2004)) (Spearman r coefficient=−0.3629, P<0.0001) (FIG. 2a,b), whereas proportion of HLA-DR positive basophils was better (Receiver Operating Characteristic (ROC) Area Under Curve (AUC)=0.9091) than anti-dsDNA IgG (ROC AUC=0.8384) to discriminate SLE subjects from healthy control (HC) (ROC AUC comparison by DeLong method (DeLong, E. R. et al., Biometrics 44, 837-845 (1988)): P=0.03) (FIG. 2c,d). Moreover, basopenia and high proportion of HLA-DR+ basophils were specific markers for active lupus nephritis when compared to other active renal diseases (FIG. 2e,f). Of note, these SLE-specific basophil parameters were independent of SLE patient treatments at the time of blood harvesting and independent of gender (data not shown). Altogether, these data validated that activated basophils, peripheral basopenia and high proportion of HLA-DR+ basophils are hallmarks of active SLE individuals. Moreover, our data strongly suggest that lupus environment drives a basophil sub-optimal activation (without a detectable degranulation response) and a basophil redistribution to SLOs.

TABLE 1

SLE Patients and control characteristics

| Variables | Lupus patients | | | | Healthy controls |
|---|---|---|---|---|---|
| | All SLE | Inactive (SLEDAI ≤ 1) | Mild (1 ≤ SLEDAI ≤ 4) | Active (SLEDAI > 4) | |
| Demographic characteristics | | | | | |
| n | 188 | 61 | 41 | 86 | 110 |
| Age, mean ± SD, years | 37.8 ± 12.3 | 43.4 ± 14.1 | 36.1 ± 10.2 | 34.7 ± 10.6 | 34.5 ± 14.9 |
| Female Gender, n (%) | 167 (89) | 51 (84) | 36 (88) | 80 (93) | 51 (47) |
| Lupus characteristics | | | | | |
| Disease duration, mean ± SD, years | 10.5 ± 8.2 | 11.7 ± 9.0 | 12.1 ± 7.5 | 9.1 ± 8.0 | — |
| Anti-dsDNA Ab positive, n (%) | 104 (55) | 10 (18) | 27 (64) | 67 (79) | — |
| History of lupus nephritis, n (%) | 144 (77) | 36 (59) | 29 (66) | 79 (92) | — |
| SLEDAI | | | | | |
| Mean ± SD | 6.6 ± 7.6 | 0.0 ± 0.2 | 2.9 ± 1.0 | 13.0 ± 6.8 | — |
| Median (range) | 4 (0-43) | 0 (0-1) | 2 (2-4) | 12 (5-43) | — |
| Treatment characteristics | | | | | |
| Current prednisone dose (mg/day) | | | | | |
| Mean ± SD | 23.6 ± 80.8 | 4.1 ± 3.9 | 7.2 ± 8.8 | 44.8 ± 115.4 | — |
| 15 mg/day or higher, n (%) | 38 (20) | 0 (0) | 4 (9) | 34 (40) | — |
| Concurrent immunosuppressive therapy (n, %) | | | | | |
| hydroxychloroquine, n (%) | 159 (84) | 54 (88) | 38 (93) | 67 (78) | — |
| mycophenolate mofetil, n (%) | 50 (27) | 15 (24) | 16 (36) | 19 (22) | — |
| cyclophosphamide, n (%) | 3 (2) | 0 (0) | 0 (0) | 3 (3) | — |
| azathioprine, n (%) | 26 (14) | 8 (13) | 7 (17) | 11 (13) | — |

SLEDAI: Systemic Lupus Erythematosus Disease Activity Index.

$PGD_2$/PTGDRs and CXCR4/CXCL12 Axes in Basophils from SLE Subjects

To decipher basophil activation and redistribution to SLOs during lupus pathogenesis, we analyzed on basophils from SLE subjects, versus HC, the expression levels of receptors for chemotactic molecules known to be dysregulated in individuals with lupus or chronic inflammatory diseases (Pellefigues, C. & Charles, N., Curr. Opin. Immunol. 25, 704-711 (2013)). Most of the screened receptor expressions were not significantly different from the ones observed on HC basophils (Table 2). Of note, Thymic Stromal Lymphopoietin Receptor (TSLP-R), IL-33 receptor (T1/ST2), C—C motif ligand receptor (CCR) 4, CCR6 and CCR7 could not be detected on basophils (Table 2).

However, PTGDR-2 expression was increased on basophils from SLE individuals (Table 2, FIG. 3a) as did its ligand titers in their plasma (11β-$PGF_2$a levels, the main plasmatic $PGD_2$ metabolite, are presented) (FIG. 3b). An inverse correlation between 11β-$PGF_2\alpha$ titers and blood basophil counts in subjects with SLE was found (Spearman r=−0.2585, P=0.0169) (data not shown). Moreover, high levels of 11β-$PGF_2\alpha$ were associated with increased basopenia in SLE subjects (FIG. 3c). Together, these data strongly suggest that $PGD_2$ and its receptors are associated with basophil activation and extravasation during lupus.

CXCR4 expression was increased on basophils from all SLE individuals, but active SLE patients showed an even more marked increase (Table 2, FIG. 3d). CXCL12 plasma titers followed the same pattern of increase as its receptor did on basophils (FIG. 3e). Basophil CXCR4 expression levels were negatively correlated with blood basophil count in SLE subjects (Spearman r=−0.4692, P<0.0001) (FIG. 4b). Moreover, in active SLE subjects, high CXCL12 titers were associated with a more pronounced basopenia (FIG. 4c). Endolyn (CD164) is a transmembrane syalomucin enhancing sensitivity to CXCL12 when associated to CXCR4 and is also known as a human basophil activation marker. CD164 levels on basophils from active SLE subjects followed the same expression pattern as CXCR4 and were correlated with basopenia (Spearman r=−0.4165, P=0.0029), suggesting an increased sensitivity of SLE basophils to CXCL12 in vivo (FIG. 3f and FIG. 4d). Basophils are known to express CXCR4 mostly intracellularly. Analyses by imaging flow cytometry showed that SLE patient basophils had an increased CXCR4 content and that it was more externalized than in HC basophils (data not shown).

TABLE 2

Basophil surface marker expression level relative to SLE disease activity

| Chemokine or cytokine receptor analyzed | CD# | Ligand(s) | Normalized expression levels (to CT mean) on basophils from: Mean (±Se, n, p Mann Whitney test vs CT) | | | |
|---|---|---|---|---|---|---|
| | | | Healthy volonteers (controls, CT) | Inactive SLE patients (SLEDAI ≤ 1) | Mild SLE patients (1 < SLEDAI ≤ 4) | Active SLE patients (SLEDAI > 4) |
| CCR1 | CD191 | CCL3, 5, 7, 23 | 1 (±0.14, 13, 1) | 1.013 (±0.17, 15, 0.78) | 1.199 (±0.13, 8, 0.40) | 1.11 (±0.18, 19, 1) |

TABLE 2-continued

Basophil surface marker expression level relative to SLE disease activity

| Chemokine or cytokine receptor analyzed | CD# | Ligand(s) | Normalized expression levels (to CT mean) on basophils from: Mean (±Se, n, p Mann Whitney test vs CT) | | | |
|---|---|---|---|---|---|---|
| | | | Healthy volunteers (controls, CT) | Inactive SLE patients (SLEDAI ≤ 1) | Mild SLE patients (1 < SLEDAI ≤ 4) | Active SLE patients (SLEDAI > 4) |
| CCR2 | CD192 | CCL2, 7, 8, 13, 16 | 1 (±0.11, 30, 1) | 1.04 (±0.15, 19, 0.89) | 1.03 (±0.25, 14, 0.57) | 1.04 (±0.2, 20, 0.58) |
| CCR3 | CD193 | Eotaxin (CCL11, 24, 26) | 1 (±0.09, 39, 1) | 0.8529 (±0.10, 10, 0.4642) | 0.9268 (±0.11, 13, 0.9663) | 0.9925 (±0.13, 20, 0.9681) |
| CCR4 | CD194 | CCL2, 4, 5, 17, 22 | ND | ND | ND | ND |
| CCR5 | CD195 | CCL5, 3, 4, 3L1 | 1 (±0.14, 6, 1) | 0.7726 (±0.09, 5, 0.43) | 1.377 (±0.42, 3, 0.38) | 1.031 (±0.19, 7, 0.94) |
| CCR6 | CD196 | CCL20 | ND | ND | ND | ND |
| CCR7 | CD197 | CCL19, 21 | ND | ND | ND | ND |
| CXCR1 | CD181 | IL-8 | 1 (±0.12, 25, 1) | 1.104 (±0.21, 6, 0.63) | 1.197 (±0.17, 6, 0.28) | 1.187 (±0.27, 13, 0.90) |
| CXCR2 | CD182 | IL-8, CXCL1, 2, 3, 5 | 1 (±0.04, 53, 1) | 1.181 (±0.12, 27, 0.85) | 0.9324 (±0.08, 15, 0.21) | 1.053 (±0.12, 37, 0.22) |
| CXCR4 | CD184 | CXCL12 | 1 (±0.04, 66, 1) | 1.317 ** (±0.09, 32, 0.0068) | 1.279 * (±0.11, 20, 0.0385) | 2.622 *** (±0.42, 51, <0.001) |
| PTGDR-2 (CRTH2) | CD294 | $PGD_2$ | 1 (±0.06, 71, 1) | 1.404 (±0.11, 48, 0.0091) ** | 1.329 * (±0.13, 31, 0.0446) | 1.328 * (±0.11, 60, 0.0493) |
| Endolyn | CD164 | CXCR4 | 1 (±0.05, 33, 1) | 1.281 * (±0.11, 15, 0.0207) | 1.158 (±0.11, 7, 0.0943) | 1.873 **** (±0.18, 26, <0.0001) |
| TSLP-R | — | TSLP | ND | ND | ND | ND |
| IL33-R | T1/ST2 | IL33 | ND | ND | ND | ND |

Abbreviations used:
SE: Standard Error;
ND: Not Detected;
CD: Cluster of Differentiation;
CT: controls;
CCL: C-C motif ligand;
CCR: C-C motif ligand receptor;
CXCL: C-X-C motif ligand;
CXCR: C-X-C motif ligand receptor;
CRTH2: Chemoattractant Receptor-homologous molecule expressed on Th2 cells (DP2, PTGDR-2);
$PGD_2$: Prostaglandin $D_2$;
PTGDR: PGD2 receptor;
TSLP: Thymic stromal lymphopoietin (-R: receptor);
Statistical analyses were by Mann-Whitney tests.
* P < 0.05,
** P < 0.01,
*** P < 0.001,
**** P < 0.0001.

CXCL12 is described as one of the most overexpressed gene during peritoneal dialysis and is actively secreted together with $PGD_2$ during peritonitis. To study human basophil migration in vivo, we analyzed them both in blood and in peritoneal dialysis fluid from patients being treated for a non-sterile peritonitis. CXCR4 expression was dramatically increased on human basophils recruited to the inflamed peritoneum as compared to their blood counterparts (data not shown). This basophil recruitment was associated with a peripheral basopenia (data not shown), as previously shown in active chronic idiopathic urticarial (Jain, S. Dermatology research and practice 2014, 674709), strongly suggesting that human CXCR4+ basophils can migrate in vivo to CXCL12- and $PGD_2$-secreting inflamed tissues, and that peripheral basopenia reflects this active basophil recruitment.

Altogether these data identified both $PGD_2$/PTGDRs and CXCL12/CXCR4 axes as basophil activation pathways during SLE flares and which may account for their associated basopenia. Therefore, these axes may contribute to the described basophil accumulation in SLOs in individuals with active lupus.

PGD2/PTGDRs Axis Enhances CXCR4-Dependent Basophil Migration During Lupus

In order to evaluate the functional consequences of the above findings, ex vivo migration assays of purified basophils from HC and active SLE subjects were performed. Strikingly, SLE basophils were attracted to CXCL12 gradients while HC basophils did not (FIG. 5a), reflecting their differences in CXCR4 and CD164 expression (FIG. 3d,f). However, no difference was detected with other common basophil chemo-attractant compounds, including $PGD_2$ (FIG. 5b). Since $PGD_2$ titers were associated with basopenia in SLE (FIG. 3c) and since autoreactive IgE are prevalent in active SLE subjects (FIG. 5c and Dema, B., et al. PLoS One 9, e90424 (2014)), we next investigated if these factors could potentiate basophil migration towards CXCL12. Standard culture of purified human basophils is known to induce intracellular CXCR4 externalization, a process inhibited in the presence of IL-3. Priming purified basophils during 18 hours with 1 µM $PGD_2$ enhanced their CXCR4 expression and their migration towards CXCL12 (FIG. 5d,e) and induced PTGDR-2 internalization (data not shown), without inducing their apoptosis (data not shown). This $PGD_2$ priming induced a slight increase in the high affinity IgE receptor alpha chain (FcεRIα) expression on basophil surface, which may increase their sensitivity to IgE-dependent stimulation (data not shown, Sub-optimal anti-IgE stimulation (Mac-Glashan, D., Jr., Clin. Exp. Allergy 40, 1365-1377 (2010)) (i) tended to increase CXCR4 expression on basophils (FIG. 5d) which may influence their migration towards CXCL12 although statistical significance was not reached (FIG. 5e), (ii) increased PTGDR-2 expression levels on basophils (FIG. 6a) and (iii) did not induce basophil degranulation (data not shown). None of other tested compounds (CCL3, CXCL2 and CCL5), known to have an effect on basophils and to be dysregulated during SLE, induced an increased CXCR4 externalization ex vivo as $PGD_2$ did (data not shown).

CXCL12 is described as one of the most overexpressed gene during peritoneal dialysis and is actively secreted together with $PGD_2$ during peritonitis. To study human basophils migration in vivo, we analyzed them both in blood and in peritoneal dialysis fluid from patients being treated for a non-sterile peritonitis. CXCR4 was found to be dramatically increased on human basophils recruited to the inflamed peritoneum as compared to their blood counterparts (FIG. 5e). This basophil recruitment was associated with a peripheral basopenia (supplementary FIG. 5b), as previously shown in active chronic idiopathic urticaria. This demonstrated that human CXCR4+ basophils can migrate in vivo to CXCL12- and $PGD_2$-secreting inflamed tissues.

We next studied the mechanism by which $PGD_2$ induced CXCR4 externalization by human basophils. Both PTGDR-1 and PTGDR-2 were cooperatively involved since antagonism of one, the other or both receptor(s) led to block CXCR4 externalization (data not shown). Moreover, blocking PTGDRs led to a decreased spontaneous CXCR4 externalization. This suggested that either ex vivo culture and/or $PGD_2$-mediated stimulation of human basophils led them to produce $PGD_2$ to have an autocrine effect as eosinophils do. To confirm this hypothesis, we used a specific H-PGDS inhibitor which resulted in the same inhibition of spontaneous CXCR4 externalization than the one induced by the PTGDR antagonists, and to a decreased PTGDR-2 internalization (data not shown). Together with the fact that the H-PGDS inhibitor effect was overcome only by a ten-fold higher $PGD_2$ concentration (data not shown), we here confirmed our above hypothesis that $PGD_2$ led to CXCR4 externalization partially by stimulating $PGD_2$ production by basophils themselves.

Altogether, these data strongly suggest that the $PGD_2$/PTGDRs axis directly influences the CXCL12 sensitivity of SLE patient basophils by increasing both their CXCR4 expression and externalization, and that lupus environment (including autoreactive IgE, CXCL12 and $PGD_2$) facilitates this cross-talk resulting in basophil extravasation and peripheral basopenia. Thus, $PGD_2$ might be required to allow CXCR4-dependent basophil migration to SLOs in SLE individuals. Indeed, both $PGD_2$/PTGDRs and CXCL12/CXCR4 axes were associated with basopenia and disease activity in lupus subjects (FIG. 3).

CXCR4/CXCL12 and $PGD_2$/PTGDRs Axes in $Lyn^{-/-}$ Lupus-Prone Mice

We previously showed that aged $Lyn^{-/-}$ mice develop a basophil-dependent $T_H2$ bias contributing to an IgE-, IL-4- and basophil-dependent lupus-like nephritis (Charles, N. et al., Nat. Med. 16, 701-707 (2010); Charles, N., et al., Immunity 30, 533-543 (2009)). In this lupus-like disease model, basophils accumulate in SLOs leading to an amplification loop of the disease (Charles, N., et al., Immunity 30, 533-543 (2009)).

We next assessed whether this mouse model was involving both CXCL12/CXCR4 and $PGD_2$/PTGDRs axes as SLE subjects did. In ex vivo migration assays, $Lyn^{-/-}$ spleen basophils migrated towards CXCL12 whereas their WT counterparts did not (FIG. 7a) mimicking the observed differences between SLE subjects and HC (FIG. 5a). CXCR4 expression levels were increased on $Lyn^{-/-}$ basophils from blood, bone marrow (BM) and SLOs as compared to their WT counterparts in aged animals (FIG. 7b). Moreover, CXCR4 expression was increased on WT and $Lyn^{-/-}$ basophils from SLOs as compared to their blood counterparts suggesting an involvement of CXCR4 in their accumulation in these organs (FIG. 7b). CXCL12 intraperitoneal (ip) injection in WT mice induced in vivo basophil migration to the injection site (FIG. 7c) and to the draining mesenteric lymph nodes (mLN) (FIG. 8a).

In vivo i.p. injection of $PGD_2$ increased CXCR4 expression on mLN Lyn basophils (FIG. 7d), as it did ex vivo on human basophils (FIG. 5d), and drove their accumulation in SLOs and peritoneum (FIG. 7e and FIG. 8b,c). Moreover, in vivo ip injection of $PGD_2$ in $Lyn^{-/-}$ mice led to a significant, but transient, peripheral basopenia when compared to steady state conditions (data not shown) as observed in peritoneal dialysis patients (data not shown). This $PGD_2$-induced basophil recruitment was strictly dependent on the CXCL12/CXCR4 axis since co-injection with AMD3100, a specific antagonist of CXCR4, completely abolished basophil recruitment both in SLOs and peritoneum (FIG. 7e and FIG. 8b,c). In mice, $PGD_2$-induced CXCR4 up-regulation was as well mediated by both PTGDR-1 and PTGDR-2 (CRTH2), as shown by the effects of their specific agonists (BW245c and DK-$PGD_2$, respectively) on spleen WT basophils ex vivo (FIG. 7f). Both agonists induced a significant but much lower increase in CXCR4 expression on other WT splenocytes including T and B cells (data not shown).

PTGDR-1 is known to induce cyclic adenosine monophosphate (cAMP) production upon engagement by $PGD_2$. We next analyzed the effect of a membrane permeable cAMP (N6,2'-O-dibutyryl-adenosine 3':5'-cyclic monophosphate (db-cAMP)) on CXCR4 externalization by mouse WT spleen basophils ex vivo. Basophils externalized CXCR4 upon db-cAMP exposure (FIG. 9a) with a 100 fold higher sensitivity than T cells to this compound (FIG. 9b). $PGD_2$ was unable to induce enough cAMP through PTGDR-1 to lead to CXCR4 externalization by T cells in these settings, unlike what was observed on basophils (FIG. 9a,b). Dose response experiments of each PTGDR specific agonists in the presence or not of H-PGDS inhibitor suggested again that both PTGDRs were able to cooperatively induce CXCR4 externalization on basophils through PTGDR-2-induced $PGD_2$ synthesis acting in an autocrine way on PTGDR-1-mediated cAMP production (FIG. 9c).

These results strongly suggest that in $Lyn^{-/-}$ old mice, as in SLE subjects, $PGD_2$ enhances in vivo CXCL12-dependent basophil accumulation in inflamed tissues and SLOs by modulating their CXCR4 expression levels through the activation of both PTGDR-1 and PTGDR-2.

PGD$_2$ Chronic Exposure Accelerates Lupus-Like Disease Development in a Basophil-Dependent Manner Therefore, a more chronic exposure to PGD$_2$ in lupus-prone mice before they start developing the disease should lead to a chronic accumulation of basophils in SLOs, an increased number of autoreactive plasma cells and to an acceleration of disease development. To verify this hypothesis, we repeatedly injected ip PGD$_2$ to young (12 weeks-old) Lyn mice every two days over ten days. As expected, basophils increased their CXCR4 expression levels (data not shown) and accumulated systemically in SLOs (FIG. 10a,b) where they were activated as shown by their increased IA-IE expression (FIG. 10c). This was associated with an increased proportion of CD19+CD138$^+$ plasma cells in SLOs (FIG. 10d,e), resulting in an increased deposition of immune complexes in the kidney as shown by C3 and IgG deposition quantification (FIG. 10f). Consequently, nearly all the PGD$_2$ injected Lyn$^{-/-}$ mice had increased albuminuria unlike their PBS-injected counterparts at the end of the protocol (FIG. 10g). Other immune cell types analyzed didn't show any significant increase in their CXCR4 surface expression (data not shown). Importantly, this PGD$_2$-induced lupus-like disease acceleration was dependent on basophils since antibody-mediated (MAR-1) basophil depletion during the whole protocol led to a complete rescue of the PGD$_2$ effects on disease development (FIG. 10b-e). These results confirmed that PGD$_2$, by enabling CXCR4-dependent basophil accumulation in SLOs, contributes to lupus-like disease and to autoantibody-mediated kidney damage.

Targeting the PGD$_2$ Axis Reduces CXCR4-Mediated Basophil Accumulation in SLOs and Dampens Lupus-Like Disease Targeting the CXCL12/CXCR4 axis in murine lupus has already been described and showed some efficacy on disease activity (Balabanian, K., et al., J. Immunol. 170, 3392-3400 (2003), Wang, A., et al., J. Immunol. 182, 4448-4458 (2009)). However, CXCR4 antagonism (with AMD3100), initially developed as an anti-HIV drug, is known to induce a release of hematopoietic stem cells and interfere with homeostatic functions (Devi, S. et al. J. Exp. Med. 210, 2321-2336, (2013), Hummel, S. et al., Curr. Opin. Hematol. 21, 29-36 (2014)). Preventing the CXCR4 up-regulation on basophils from lupus-prone Lyn$^{-/-}$ mice by blocking the PGD$_2$/PTGDRs axis seemed a safer approach to disable the basophil-dependent amplification loop of autoantibody production in SLOs.

Then, we treated aged Lyn and WT mice by oral gavage with both specific antagonists of PTGDR-1 and PTGDR-2, Laropiprant and CAY10471, respectively, at a dose of 5 mg/kg each, twice daily for ten days. This treatment led to a dramatic reduction in basophil numbers in SLOs of Lyn$^{-/-}$ animals (FIG. 12a,b) associated with a decreased CXCR4 expression on spleen basophils (FIG. 12c). Of note, BM and blood basophil proportions were not affected by the treatment (FIG. 13a,b). These results validated the approach consisting of disabling basophil accumulation in SLOs by targeting the PTGDRs.

As expected, this reduction in basophil accumulation was associated with a significant decrease of CD19$^+$CD138$^+$ short-lived plasma cell numbers (FIG. 12d and FIG. 13c). Strikingly, proportions of all other immune cell populations analyzed (B cells, neutrophils, Ly6C$^+$ monocytes, and Ly6C$^-$ monocytes) remained unaffected by the treatment as did their CXCR4 expression levels (data not shown). PTGDRs blockade in Lyn$^{-/-}$ animals, by disabling basophil accumulation in SLOs, decreased their autoantibody titers (FIG. 12e and FIG. 13d) and their T$_H$2 bias as measured by total IgE plasma concentrations (FIG. 12f). Consequently, this treatment allowed as well a significant decrease in the kidney content of C3 and IgG deposits (FIG. 11) and the pro-inflammatory cytokines IL-4 and IL-1β (FIG. 12g,h). Therefore, a short-term treatment with PTGDRs antagonists allowed an efficient dampening in the disease activity observed in our lupus-prone animals.

Altogether, these results suggest that aiming the PGD$_2$/PTGDRs axis could be a valuable new therapeutic approach in SLE. Indeed, PTGDRs blockade, by breaking the CXCL12-dependent basophil homing to SLOs, might turn-off the basophil-dependent amplification loop of autoantibody production, efficiently preventing flares and subsequent organ damage in SLE (FIG. 14).

The invention claimed is:

1. A method for treating lupus nephritis in a patient in need thereof, wherein said method comprises administering said patient with a PTGDR-1 antagonist in an amount sufficient to limit an extent or reduce an occurrence of organ damage.

2. The method according to claim 1, wherein said antagonist is a small molecule antagonist.

3. The method according to claim 1, wherein said antagonist has formula (I)

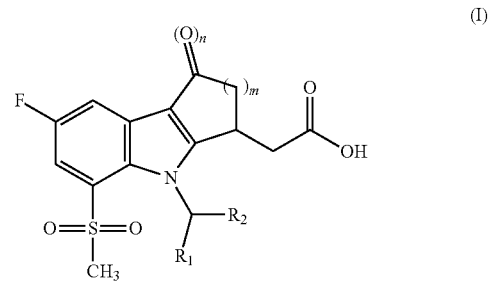

or pharmaceutically acceptable salts thereof, wherein n is 0 or 1; m is 1, 2 or 3; R$_1$ is H, C$_1$-C$_3$ alkyl, halogenated C$_1$-C$_3$ alkyl or cyclopropyl; R$_2$ is 4-chlorophenyl or 2,4,6-trichlorophenyl.

4. The method according to claim 1, wherein said PTGDR-1 antagonist is laropiprant.

5. The method according to claim 1, wherein said PTGDR-1 antagonist is used in combination with at least a PTGDR-2 antagonist.

6. The method according to claim 5, wherein said PTGDR-2 antagonist has formula (VIII)

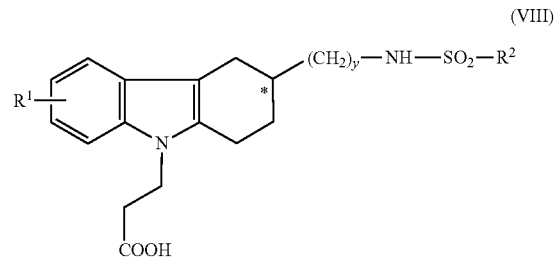

wherein R1 is H, fluorine, methyl, methoxy, benzyloxy, or hydroxyl,

R2 is phenyl which is substituted by fluorine, chlorine, trifluoromethyl, methyl, ethyl, propyl, isopropyl, or methoxy, and Y is 0 or 1, or pharmaceutically acceptable salts thereof.

7. The method according to claim 6, wherein said PTGDR-2 antagonist is CAY10471 (TM30089).

8. The method according to claim 5, wherein said PTGDR-1 antagonist and PTGDR-2 antagonist are formulated in a single pharmaceutical composition.

9. The method according to claim 5, wherein said PTGDR-1 antagonist and PTGDR-2 antagonist are formulated in separate pharmaceutical compositions for simultaneous use, separate use, or use spread over time.

10. A method for treating lupus nephritis in a patient in need thereof, wherein said method comprises administering said patient with a pharmaceutical composition comprising a PTGDR-1 antagonist and a PTGDR-2 antagonist, or a dual PTGDR-1/PTGDR-2 antagonist in an amount sufficient to limit an extent or reduce an occurrence of organ damage.

11. A method for treating lupus nephritis in a patient in need thereof, wherein said method comprises administering said patient with a PTGDR-1 antagonist and a PTGDR-2 antagonist as a combined preparation for simultaneous use, separate use, or use spread over time.

12. A method for treating lupus nephritis in a patient in need thereof, wherein said method comprises administering said patient with a PTGDR-2 antagonist.

13. The method according to claim 1 wherein the PTGDR-1 antagonist prevents basophil homing to secondary lymphoid organs.

14. The method according to claim 1 wherein the PTGDR-1 antagonist prevents, limits the extent or reduces the increase in autoantibody titers and/or the occurrence of SLE flares and/or organ damages.

\* \* \* \* \*